United States Patent
Ivosevic

(10) Patent No.: US 12,329,523 B2
(45) Date of Patent: Jun. 17, 2025

(54) BLOOD COLLECTION ASSEMBLY WITH VIBRATION MODULE

(71) Applicant: Becton, Dickinson and Company, Franklin Lakes, NJ (US)

(72) Inventor: Milan Ivosevic, Kinnelon, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 777 days.

(21) Appl. No.: 17/057,327

(22) PCT Filed: May 22, 2019

(86) PCT No.: PCT/US2019/033493
§ 371 (c)(1),
(2) Date: Nov. 20, 2020

(87) PCT Pub. No.: WO2019/226754
PCT Pub. Date: Nov. 28, 2019

(65) Prior Publication Data
US 2021/0196164 A1    Jul. 1, 2021

Related U.S. Application Data

(60) Provisional application No. 62/676,325, filed on May 25, 2018.

(51) Int. Cl.
*A61B 5/15* (2006.01)
*A61B 5/151* (2006.01)

(52) U.S. Cl.
CPC .. *A61B 5/150022* (2013.01); *A61B 5/150068* (2013.01); *A61B 5/150083* (2013.01);
(Continued)

(58) Field of Classification Search
CPC ........ A61B 5/150022; A61B 5/150068; A61B 5/150083; A61B 5/150343;
(Continued)

(56) References Cited

U.S. PATENT DOCUMENTS 6,071,250 A    6/2000 Douglas et al.
6,231,531 B1 *  5/2001 Lum ................ A61B 5/150137
                                              600/583

(Continued)

FOREIGN PATENT DOCUMENTS

CN    103826686 A    5/2014
DE    10315396 A1    10/2004
(Continued)

*Primary Examiner* — Jennifer Robertson
*Assistant Examiner* — Elina Sohyun Jang
(74) *Attorney, Agent, or Firm* — The Webb Law Firm

(57) ABSTRACT

A device (1) for obtaining a biological sample that includes a blood collection device (10) and a vibration device (80) removably attachable to the blood collection device that provides pain relief is disclosed. The vibration device of the present disclosure provides pain relief to a patient by vibrating the blood collection device. The vibration device can be attached to the blood collection device before it is placed onto a finger to provide pain relief during the finger lancing as well as to aid blood flow from the finger into a collection container during the collection process.

26 Claims, 18 Drawing Sheets

(52) U.S. Cl.
CPC .. *A61B 5/150137* (2013.01); *A61B 5/150267* (2013.01); *A61B 5/150343* (2013.01); *A61B 5/150732* (2013.01); *A61B 5/150748* (2013.01); *A61B 5/15144* (2013.01); *A61B 5/15194* (2013.01)

(58) Field of Classification Search
CPC ........ A61B 5/150389; A61B 5/150061; A61B 5/14532; A61B 5/150412; A61B 5/15194; A61B 5/15186; A61B 5/15117; A61B 5/150114; A61B 5/150519; A61B 5/15087; A61B 5/157; A61B 5/150137; A61B 5/150267; A61B 5/150732; A61B 5/150748; A61B 5/15144; A61B 5/15109; A61B 5/14546; A61B 5/150351; A61B 5/150358; A61B 5/150717; A61B 5/15113; A61B 5/1519; A61B 5/6826; A61B 5/6838; A61B 5/6839; A61B 5/6842; A61B 2562/0295; A61B 5/1411; A61B 5/150167; A61B 5/15142; A61M 5/422

See application file for complete search history.

(56) References Cited

U.S. PATENT DOCUMENTS

| | | | |
|---|---|---|---|
| 6,925,317 | B1* | 8/2005 | Samuels ............. A61B 5/6833 600/344 |
| 8,057,404 | B2 | 11/2011 | Fujiwara et al. |
| 9,380,975 | B2 | 7/2016 | Karbowniczek et al. |
| 10,610,142 | B1 | 4/2020 | Diju et al. |
| 2002/0022789 | A1 | 2/2002 | Perez et al. |
| 2006/0052809 | A1 | 5/2006 | Karbowniczek et al. |
| 2006/0155316 | A1* | 7/2006 | Perez ................ A61B 5/150412 600/583 |
| 2008/0086063 | A1 | 4/2008 | Baxter et al. |
| 2009/0198152 | A1 | 8/2009 | Kim |
| 2009/0259145 | A1 | 10/2009 | Bartfeld et al. |
| 2009/0298106 | A1* | 12/2009 | Hooper ............ A61B 5/150305 435/26 |
| 2011/0118568 | A1* | 5/2011 | Sei .................... A61B 5/150717 600/309 |
| 2012/0029422 | A1 | 2/2012 | Goldberg et al. |
| 2015/0351676 | A1 | 12/2015 | Faurie et al. |
| 2016/0262367 | A1* | 9/2016 | Sandford ............. A01M 1/145 |
| 2019/0099117 | A1 | 4/2019 | Pulitzer et al. |
| 2019/0371136 | A1 | 12/2019 | Whitaker |

FOREIGN PATENT DOCUMENTS

| | | |
|---|---|---|
| EP | 0224650 A2 | 6/1987 |
| EP | 1157660 A1 | 11/2001 |
| EP | 1535572 A1 | 1/2005 |
| EP | 2184012 A1 | 5/2010 |
| EP | 2243427 A1 | 10/2010 |
| GB | 2183159 A | 6/1987 |
| GB | 2409411 A | 6/2005 |
| JP | 2000146777 A | 5/2000 |
| JP | 2002219115 A | 8/2002 |
| JP | 2005176924 A | 7/2005 |
| JP | 200668384 A | 3/2006 |
| WO | 2004064637 A1 | 8/2004 |
| WO | 2008027319 A2 | 3/2008 |
| WO | 2009081405 A2 | 7/2009 |
| WO | 2009145920 A1 | 12/2009 |
| WO | 2015048157 A1 | 4/2015 |
| WO | 2018039305 A1 | 3/2018 |
| WO | 2018039307 A1 | 3/2018 |

* cited by examiner

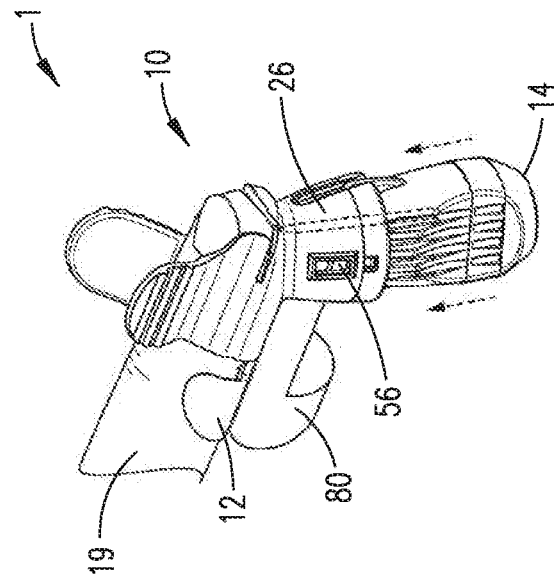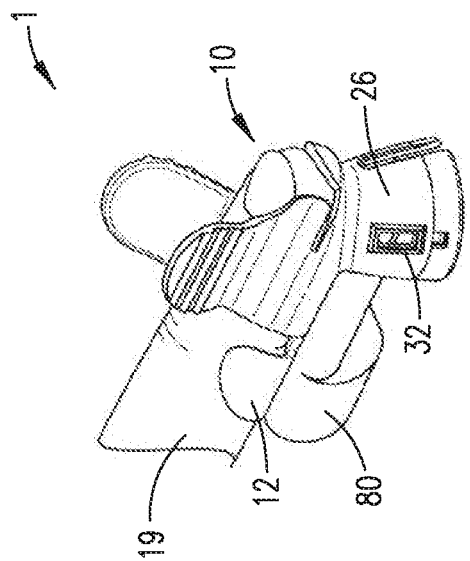

BLOOD COLLECTION ASSEMBLY WITH VIBRATION MODULE

CROSS-REFERENCE TO RELATED APPLICATIONS

This application is the United States national phase of International Application No. PCT/US2019/033493 fed May 22, 2019, and claims priority to U.S. Provisional Application Ser. No. 62/676,325, entitled "Blood Collection Assembly with Vibration Module" filed May 25, 2018, the disclosures of which are hereby incorporated by reference in their entirety.

BACKGROUND OF THE INVENTION

1. Field of the Disclosure

The present disclosure relates generally to a device for obtaining a biological sample. More particularly, the present disclosure relates to an integrated finger-based capillary blood collection device with the ability to lance and squeeze a finger, collect, stabilize, and dispense a blood sample in a controlled manner while also providing pain relief.

2. Description of the Related Art

Devices for obtaining and collecting biological samples, such as blood samples, are commonly used in the medical industry. One type of blood collection that is commonly done in the medial field is capillary blood collection which is often done to collect blood samples for testing. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests. Various types of lancet devices have been developed which are used for puncturing the skin of a patient to obtain a capillary blood sample from the patient. The blood sample that is received is then collected and/or tested. This testing can be done by a Point-of-Care (POC) testing device or it can be collected and sent to a testing facility.

Many different types of lancet devices are commercially available to hospitals, clinics, doctors' offices, and the like, as well as to individual consumers. Such devices typically include a sharp-pointed member such as a needle, or a sharp-edged member such as a blade, that is used to make a quick puncture wound or incision in the patient's skin in order to provide a small outflow of blood. It is often physiologically and psychologically difficult for many people to prick their own finger with a hand-held needle or blade. As a result, lancet devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example, on the finger. Often, a spring is incorporated into the device to provide the "automatic" force necessary to puncture or cut the skin of the patient.

Currently, capillary blood collection workflow is a complex multi-step process requiring high skill level. The multi-step nature of this process introduces several variables that could cause sample quality issues such as hemolysis, inadequate sample stabilization, and micro-clots. The use of lancet devices for obtaining blood samples can result in several variables that effect the collection of the capillary blood sample, including, but not limited to, holding the lancet still during the testing, obtaining sufficient blood flow from the puncture site, adequately collecting the blood, preventing clotting, and the like.

When large capillary sample volumes are required, e.g., 300-500 µL, capillary blood collection workflow requires an even more complex multi-step process that requires a high skill level such as a trained nurse or phlebotomist. A large capillary sample volume also requires a deeper cut using lancets with the largest blades that cut deep into a fingertip causing sharp pain due to a dense capillary bed with a lot of nerve endings at the fingertips. Moreover, there is also significant patient discomfort due to intense manual finger squeezing, i.e., milking, of the blood from a patient's finger that could go for several minutes and leave bruises when extracting large blood volumes.

Thus, there is a need in the art for a device that has the ability to lance and squeeze the finger, collect the sample, stabilize the sample, and subsequently dispense the sample in a controlled manner while also providing pain relief to a patient.

SUMMARY OF THE INVENTION

The present disclosure is directed to a device for obtaining a biological sample that includes a blood collection device and a vibration device removably attachable to the blood collection device that provides pain relief. Advantageously, the vibration device of the present disclosure provides pain relief to a patient by vibrating the blood collection device. The vibration device can be attached to the blood collection device before it is placed onto a finger to provide pain relief during the finger lancing as well as to aid blood flow from the finger into a collection container during the collection process.

A vibration device of the present disclosure provides pain relief to a patient during use of a blood collection device by de-sensitizing skin via mechanical vibrations that stimulate $A_\beta$ peripheral nerve fibers and mask pain signals sent to the brain during a finger lancing process. Additionally, the mechanical vibrations in combination with controlled gentle finger massaging using a blood collection device of the present disclosure reduces patient discomfort during a blood extraction process as well as speeds up the collection by stimulating an efficient blood flow through the capillary beds and out of the finger.

In accordance with an embodiment of the present invention, a device for obtaining a blood sample includes a blood collection device and a vibration device removably attachable to the blood collection device, wherein the blood collection device is disposable and the vibration device is reusable.

In one configuration, the vibration device is transitionable between an off position and an on position. In another configuration, with the vibration device attached to the blood collection device and the vibration device in the on position, the vibration device vibrates the entire blood collection device. In yet another configuration, the vibration device is attached to the blood collection device via a mechanical connection. In one configuration, the vibration device is attached to the blood collection device via a magnetic connection.

In accordance with another embodiment of the present invention, a device for obtaining a blood sample includes a blood collection device having an inlet, an interior, and a puncturing element moveable between a pre-actuated position wherein the puncturing element is retained within the interior and a puncturing position wherein at least a portion of the puncturing element extends through the inlet and a vibration device removably attachable to the blood collection device.

In one configuration, the vibration device is transitionable between an off position and an on position. In another configuration, with the vibration device attached to the blood collection device and the vibration device in the on position, the vibration device vibrates the entire blood collection device. In yet another configuration, the vibration device is attached to the blood collection device via a mechanical connection. In one configuration, the vibration device is attached to the blood collection device via a magnetic connection.

In accordance with another embodiment of the present invention, a device for obtaining a blood sample includes a holder for receiving a sample source, the holder having an actuation portion and a port; a lancet housing secured within the port, the lancet housing having an inlet and an interior, a puncturing element moveable between a pre-actuated position wherein the puncturing element is retained within the interior and a puncturing position wherein at least a portion of the puncturing element extends through the inlet; a container removably connectable to a portion of the lancet housing, the container defining a collection cavity; and a vibration device removably connectable to a portion of the holder.

In one configuration, the actuation portion is transitionable between a first position in which the holder defines a first ellipse and a second position in which the holder defines a second ellipse, wherein the second ellipse is different than the first ellipse. In another configuration, the actuation portion includes a pumping member for applying pressure to the sample source. In yet another configuration, the pumping member comprises a pair of opposed tabs. In one configuration, the sample source is a finger. In another configuration, with the finger received within the holder, the port is in communication with a portion of the finger. In yet another configuration, the lancet housing includes an outlet. In one configuration, with the container connected to the lancet housing, the outlet of the lancet housing is in fluid communication with the collection cavity of the container. In another configuration, with the finger received within the holder and the puncturing element in the puncturing position, the puncturing element lances the finger to draw the blood sample. In yet another configuration, the blood sample is received within the collection cavity of the container. In one configuration, the vibration device is transitionable between an off position and an on position. In another configuration, with the vibration device connected to the holder and the vibration device in the on position, the vibration device vibrates the entire device for obtaining the blood sample. In yet another configuration, the vibration device is attached to the holder via a mechanical connection. In one configuration, the vibration device is attached to the holder via a magnetic connection.

In accordance with another embodiment of the present invention, a device for obtaining a blood sample includes a holder for receiving a sample source, the holder having an actuation portion and a vibration device removably connectable to a portion of the holder, wherein the actuation portion is transitionable between a first position in which the holder defines a first ellipse and a second position in which the holder defines a second ellipse, wherein the second ellipse is different than the first ellipse.

In one configuration, the vibration device is transitionable between an off position and an on position. In another configuration, with the vibration device connected to the holder and the vibration device in the on position, the vibration device vibrates the entire device for obtaining the blood sample. In yet another configuration, the actuation portion includes a pumping member for applying pressure to the sample source. In one configuration, the pumping member comprises a pair of opposed tabs. In another configuration, the sample source is a finger.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 21 is a perspective view of a first step of using a vibration device and blood collection device of the present disclosure in accordance with an embodiment of the present invention.

FIG. 22 is a perspective view of a second step of using a vibration device and blood collection device of the present disclosure in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
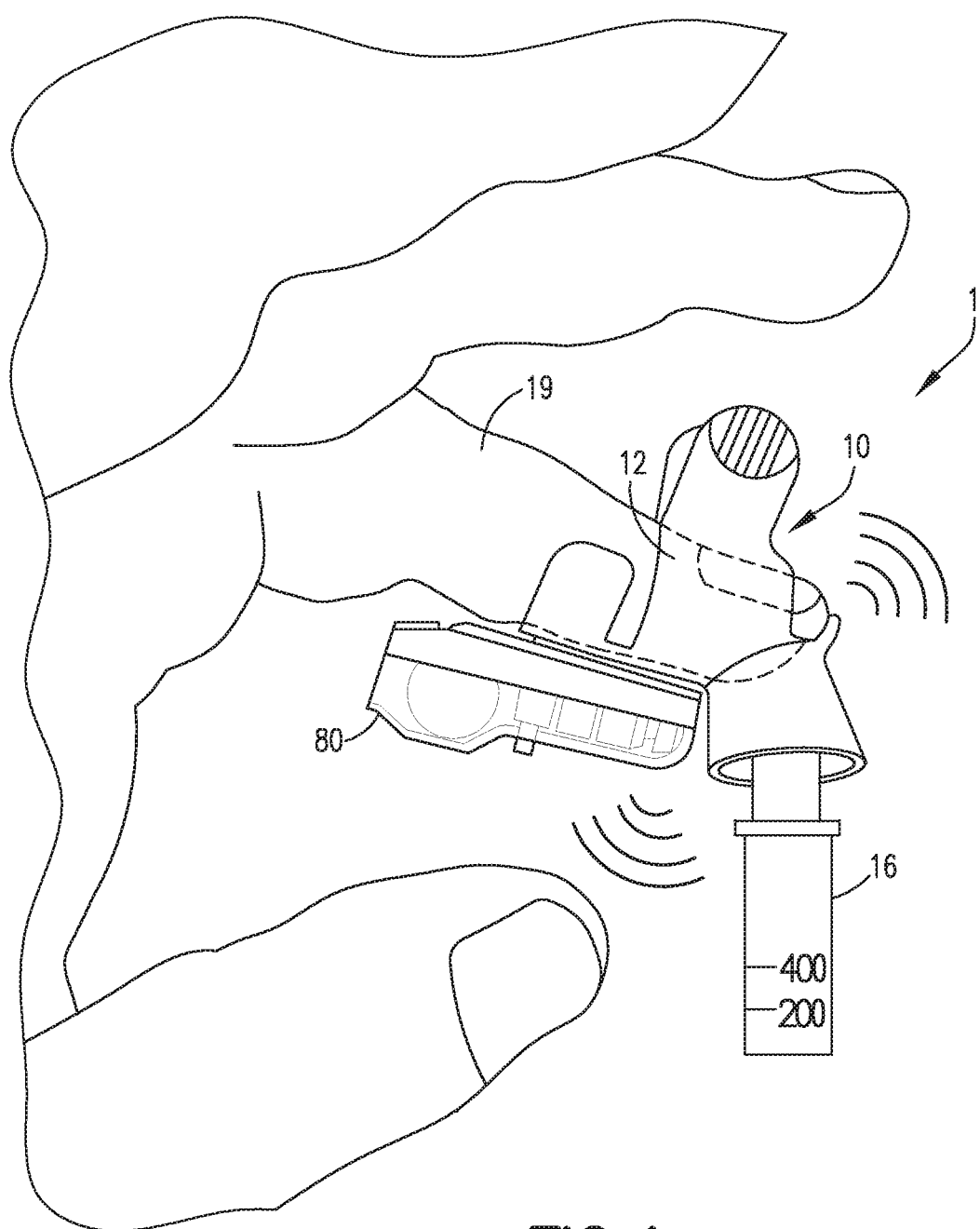
FIG. 1 is a perspective view of a vibration device and blood collection device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to a device for obtaining a biological sample that includes a blood collection device and a vibration device removably attachable to the blood collection device that provides pain relief. The vibration device can be attached to the blood collection device before it is placed onto a finger to provide pain relief during the finger lancing as well as to aid blood flow from the finger into a collection container during the collection process.

A vibration device of the present disclosure provides pain relief to a patient during use of a blood collection device by de-sensitizing skin via mechanical vibrations that stimulate $A_\beta$ peripheral nerve fibers and mask pain signals sent to the brain during a finger lancing process. Additionally, the mechanical vibrations in combination with controlled gentle finger massaging using a blood collection device of the present disclosure reduces patient discomfort during a blood extraction process as well as speeds up the collection by stimulating an efficient blood flow through the capillary beds and out of the finger.

Referring to FIGS. 1-6 and 21-25, in an exemplary embodiment, a device 1 for obtaining a blood sample 18 includes a blood collection device 10 and a vibration device 80 that is removably attachable to the blood collection device 10. In an exemplary embodiment, the blood collection device of the present disclosure includes a holder 12, a lancet 14, and a collection container 16 as described in more detail below.

When a large capillary sample volume from a patient is required, e.g., 300-500 μL, a deeper cut is required using lancets with the largest blades that cut deep into a fingertip causing sharp pain due to a dense capillary bed with a lot of nerve endings at the fingertips. Moreover, there is also significant patient discomfort due to intense manual finger squeezing, i.e., milking, of the blood from a patient's finger that could go for several minutes and leave bruises when extracting large blood volumes.

Advantageously, the vibration device 80 of the present disclosure provides pain relief to a patient by vibrating the blood collection device 10. In an exemplary embodiment, the vibration device 80 can be attached to the blood collection device 10 before it is placed onto a finger 19 of a patient to provide pain relief during the finger lancing as well as to aid blood flow from the finger 19 into a collection container 16 during the collection process.

In one embodiment, the vibration device 80 of the present disclosure is an electrical vibrator that is removably attachable to a portion of the blood collection device 10. For example, in one embodiment, the vibration device 80 is removably attachable to the holder 12 of the blood collection device 10. In other embodiments, the vibration device 80 may be removably attachable to other portions of the blood collection device 10. In other embodiments, it is envisioned that the vibration device 80 of the present disclosure can be other types of vibrators that provide vibrations to the blood collection device 10. In an exemplary embodiment, the vibration device 80 is transitionable between an off position in which no vibrations are transmitted from the vibration device 80 and an on position in which vibrations are transmitted from the vibration device 80.

It is noted that the vibrational frequency of the vibration device 80 could range from between less than 10 Hz to 1,000 Hz, such as 10 Hz to 1,000 Hz, and in certain cases between 30 to 120 Hz. The vibration device 80 can be configured to produce continuous vibrations within this range, or to provide variable vibration cycles with periods of higher frequency interposed between periods of lower frequency, or periods of vibration interposed between periods of non-vibration.

In a further configuration, the vibration device 80 may be activated or turned on by the action of attaching the vibration device 80 to the holder 12 or other portion of the collection device 10. Similarly, the vibration device may also be deactivated or turned off by the action of decoupling the vibration device 80 from the holder 12 or other portion of the collection device 10. It is noted herein that the vibration device 80 may be coupled mechanically, electrically, or magnetically to achieve this activation and/or deactivation.

Figure 2:
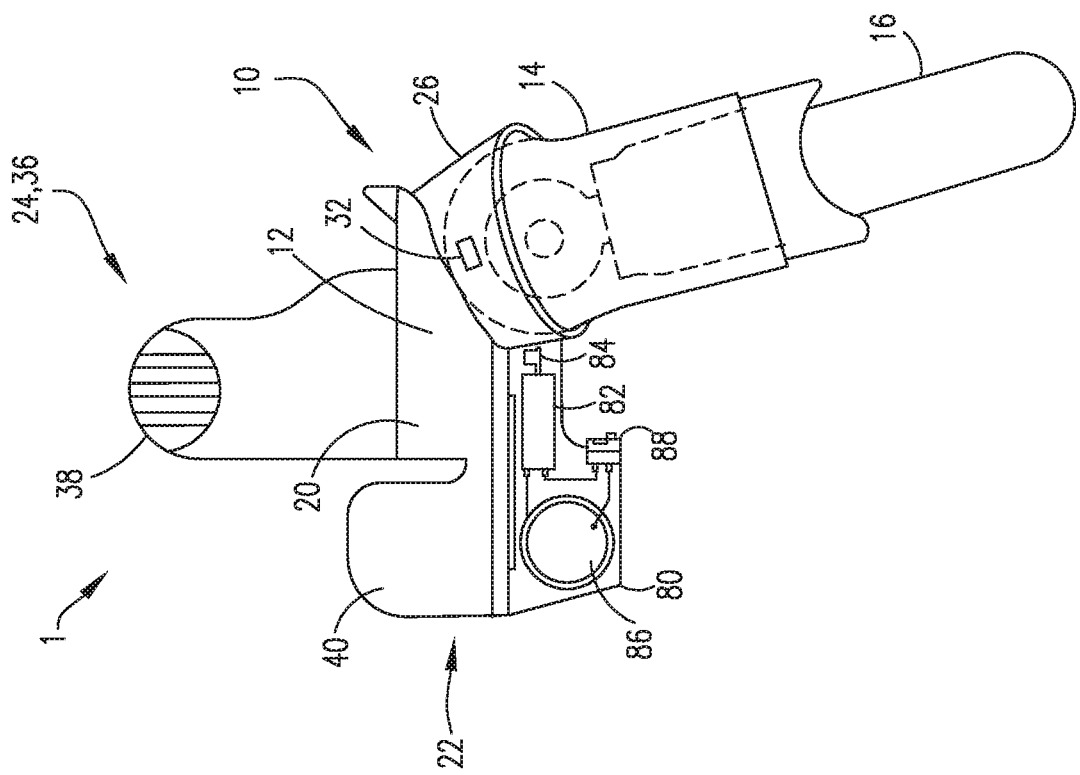
FIG. 2 is a perspective view of a vibration device removed from a blood collection device in accordance with an embodiment of the present invention.
Figure 3:
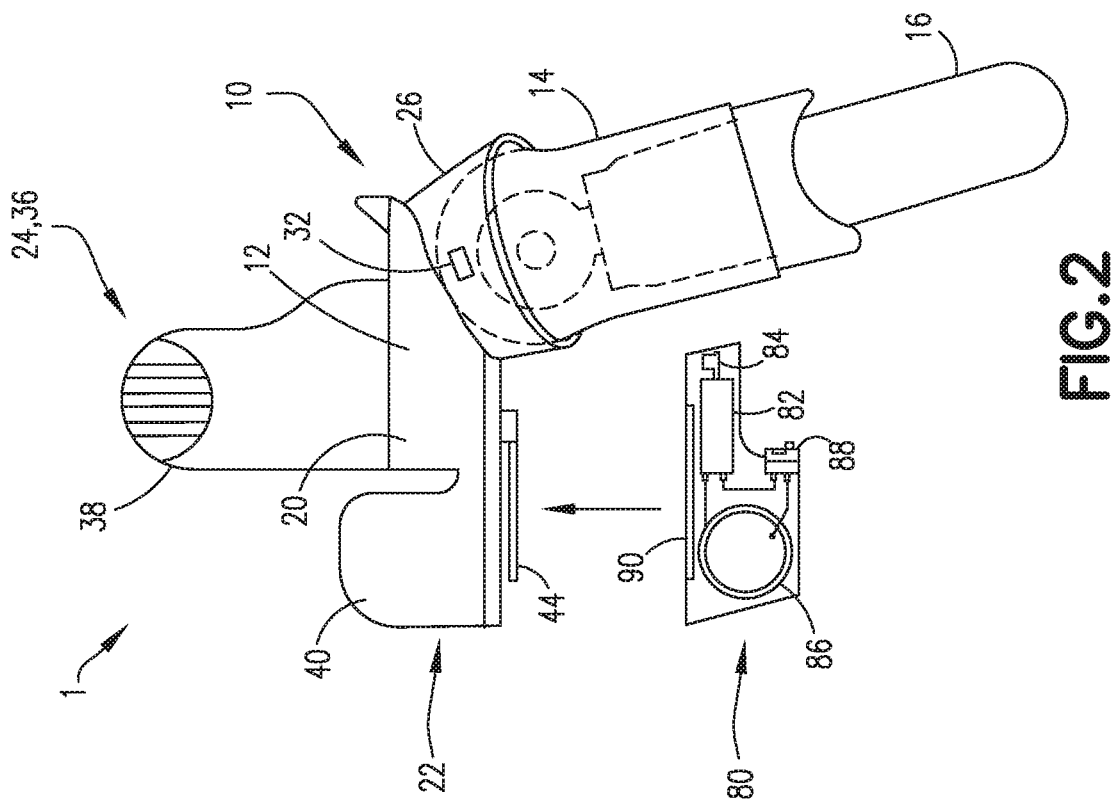
FIG. 3 is a perspective view of a vibration device attached to a blood collection device in accordance with an embodiment of the present invention.

Referring to FIGS. 2 and 3, the vibration device 80 of the present disclosure is removably attachable to a portion of the blood collection device 10. For example, in one embodiment, the vibration device 80 includes a vibration connection portion 90, and a portion of the blood collection device 10, e.g., the holder 12, includes a connection portion 44. The vibration connection portion 90 is removably attachable to the connection portion 44 of the blood collection device 10. In this manner, the vibration device 80 can be easily and quickly secured to the blood collection device 10 and removed from the blood collection device 10. In one embodiment, the vibration connection portion 90 and the connection portion 44 of the blood collection device 10 include components forming a mechanical connection. In another embodiment, the vibration connection portion 90 and the connection portion 44 of the blood collection device 10 include components forming a magnetic connection. In other embodiments, it is envisioned that the vibration connection portion 90 and the connection portion 44 of the blood collection device 10 include components forming other connection mechanisms.

When the vibration device 80 is turned on, the vibration device 80 causes the blood collection device 10 to vibrate. In this manner, the vibrations from the vibration device 80 are transmitted to the blood collection device 10 and then to the patient, e.g., a finger 19 of the patient, which desensitizes skin by stimulating large and fast AP peripheral nerve fibers (FIG. 7).

Figure 7:
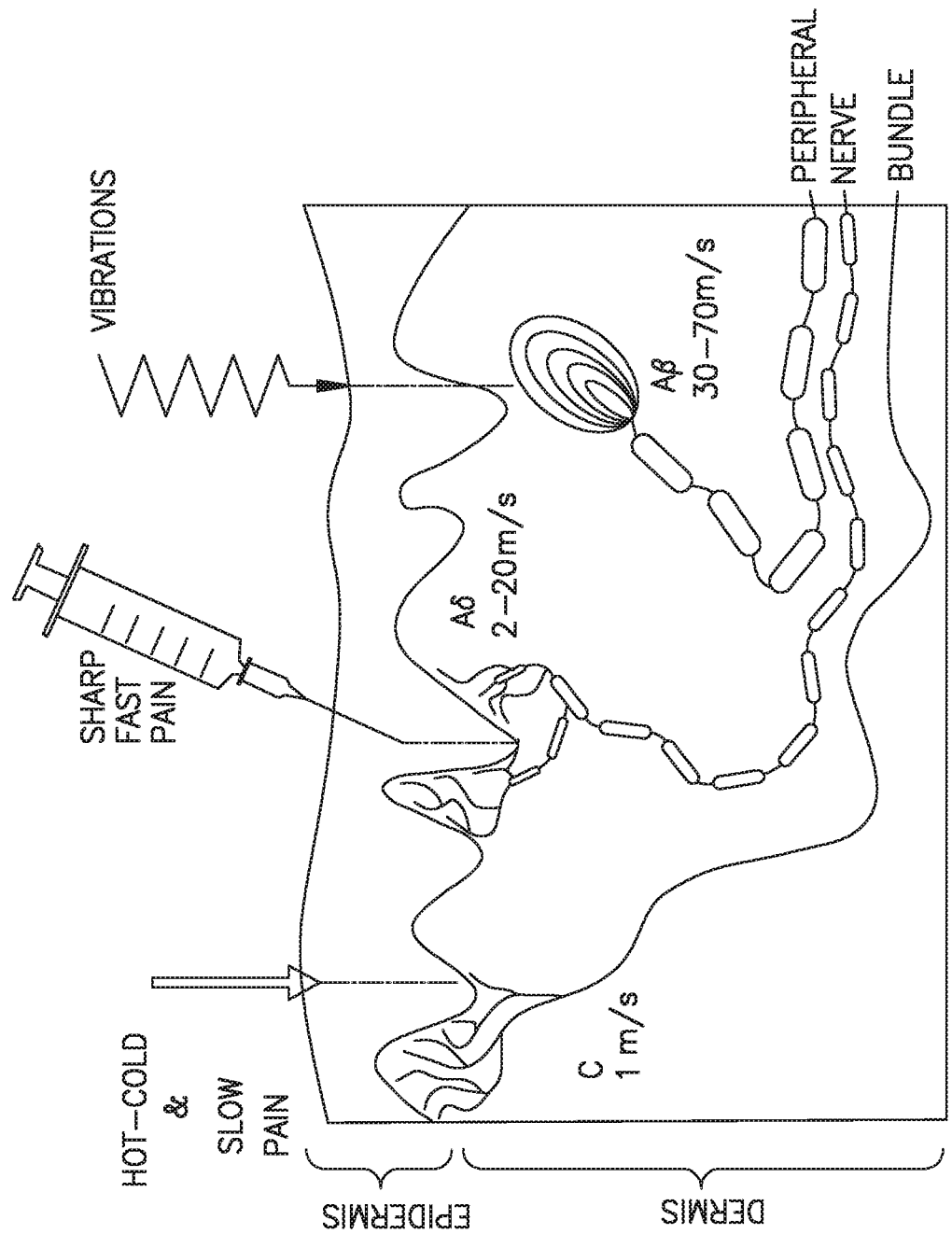
FIG. 7 is a schematic representation of a pain signal from a lancet cut mixed together with a vibration signal from a vibration device being simultaneously sent to a patient in accordance with an embodiment of the present invention.
Figure 16:
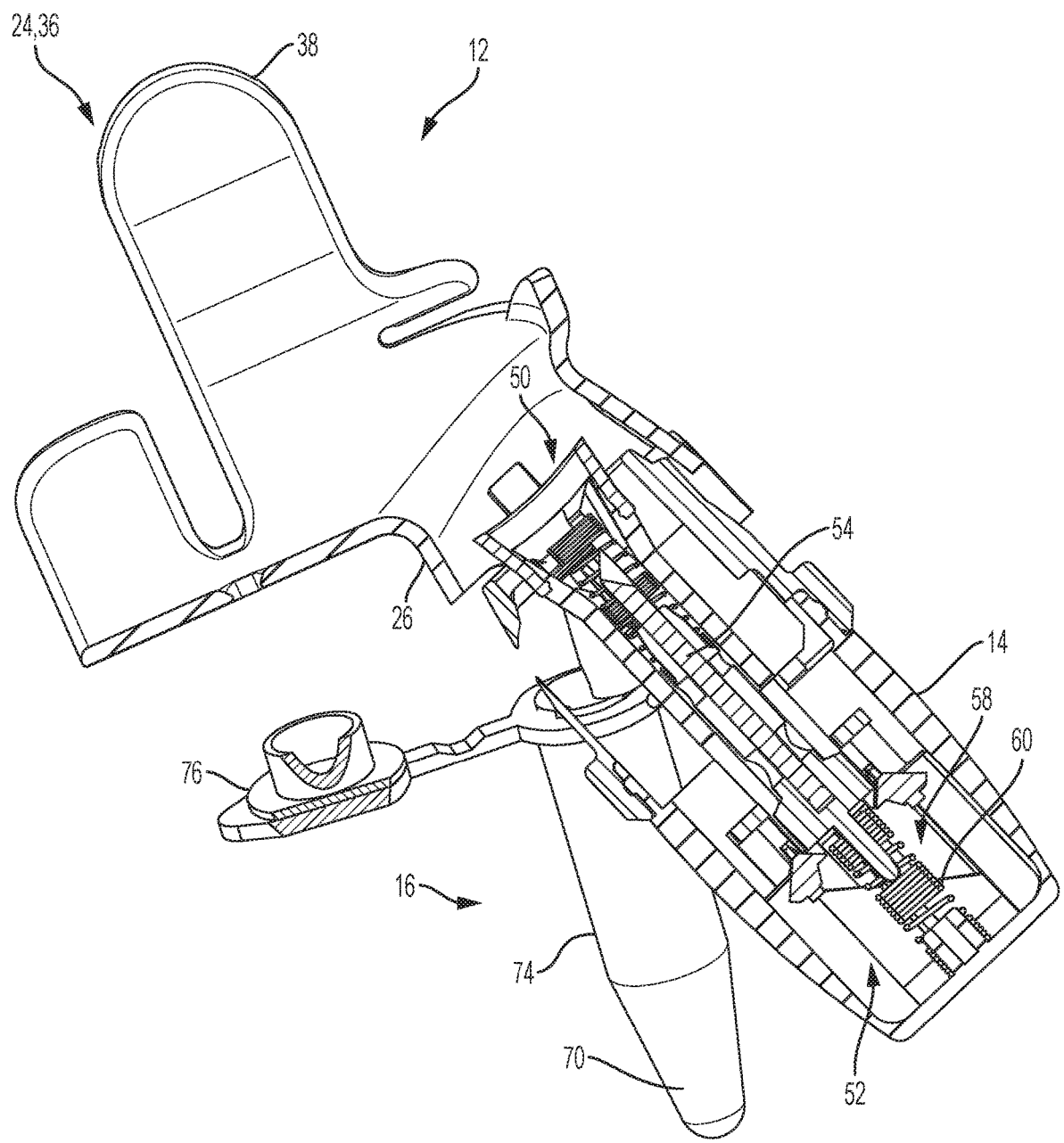
FIG. 16 is a cross-sectional view of a blood collection device of FIG. 14 in accordance with another embodiment of the present invention.

Referring to FIG. 7, to collect blood from the finger 19 of the patient, a puncturing element 54 (FIGS. 16-18) of the lancet 14 cuts into the finger 19 of the patient causing sharp pain due to a dense capillary bed with a lot of nerve endings at the fingertips. By having the vibration device 80 turned on and providing vibrations to the blood collection device 10 and the finger 19 of the patient simultaneously with the puncturing element 54 of the lancet 14 cutting the finger 19 of the patient causing sharp pain, the vibration signals sent to the finger 19 of the patient and the pain nerve signals from the lancet cut are mixed together. In this manner, the vibration signals are able to mask the overall pain signal to the brain, provide a different sensation experience, and often a perception of lower pain thereby providing a patient pain relief during finger lancing.

In one embodiment, the vibration device 80 of the present disclosure provides pain relief by mechanically vibrating the blood collection device 10. In one embodiment, the vibration device 80 of the present disclosure provides pain relief to a patient by vibrating the entire blood collection device 10.

In an exemplary embodiment, the vibration device 80 of the present disclosure can be attached to the blood collection device 10 before the blood collection device 10 is placed onto a finger 19 of a patient. In other exemplary embodiments, the vibration device 80 of the present disclosure can be attached to the blood collection device 10 with the blood collection device 10 on a finger 19 of a patient before a lancing of the finger 19.

In one configuration, the vibration device 80 may be activated to provide vibrational stimulus to the lancing portion of a patient for up to 120 seconds or longer prior to lancing of the patient, such as at a tip of a patient finger. In certain lancing situations, the vibration device 80 may be activated to provide vibrational stimulus to the lancing portion of a patient for between 5 and 20 seconds prior to lancing of the patient. This vibrational time period allows the vibration device 80 to activate vibrational analgesia in most patients. It is also noted herein that the vibrational device 80 should be maintained in the activated state throughout the specimen and/or blood collection process. This typically does not exceed a period of 3 minutes, and may be completed in less than 2 minutes.

Referring to FIGS. 1-6, in one embodiment, the vibration device 80 of the present disclosure is an electrical vibrator that is removably attachable to a portion of the blood collection device 10, e.g., a portion of the holder 12. In an exemplary embodiment, the vibration device 80 of the present disclosure includes an electrical motor 82 with eccentric flywheel 84 to produce vibrations, a battery 86, and a switch 88 that transitions the vibration device 80 between an off position and an on position. In some embodiments, it is envisioned that the battery 86 of the vibration device 80 is approximately a 1.5V-3V battery.

In one embodiment, the electrical motor 82 of the vibration device 80 is an AC or DC motor with eccentric flywheel 84 in different motor configurations. The electrical motor 82 of the vibration device 80 can have constant or variable vibrational frequency. In some embodiments, the vibration device 80 may include an electronic module that controls the vibrator frequency and maintains the vibrations in a predefined range or even to match resonant frequency of an entire device on the finger 19 during the collection process.

In one embodiment, the blood collection device 10 of the present disclosure is disposable and the vibration device 80 of the present disclosure is reusable. For example, the holder 12, the lancet 14, and the collection container 16 of the blood collection device 10 may be disposed of after use. The vibration device 80 can be removed from a blood collection device 10 after use and saved for later use with additional disposable blood collection devices 10.

Referring to FIGS. 2-6 and 21-25, use of a vibration device 80 of the present disclosure will now be described.

Referring to FIG. 2, in one embodiment, the vibration device 80 is attached to the blood collection device 10 before the holder 12 of the blood collection device 10 is placed onto a finger 19 of a patient. Next, referring to FIGS. 4, 21, and 22, the vibration device 80 is turned to the on position to vibrate the blood collection device 10 and the finger 19 of the patient before lancing the finger 19 using the puncturing element 54 of the lancet 14. The vibration device 80 is kept on to provide vibrations to the blood collection device 10 and the finger 19 of the patient until the blood collection is completed. For example, referring to FIG. 22, by having the vibration device 80 turned on and providing vibrations to the blood collection device 10 and the finger 19 of the patient simultaneously with the puncturing element 54 of the lancet 14 cutting the finger 19 of the patient causing sharp pain, the vibration signals sent to the finger 19 of the patient and the pain nerve signals from the lancet cut are mixed together. In this manner, the vibration signals are able to mask the overall pain signal to the brain, provide a different sensation experience, and often a perception of lower pain thereby providing a patient pain relief during finger lancing.

Figure 5:
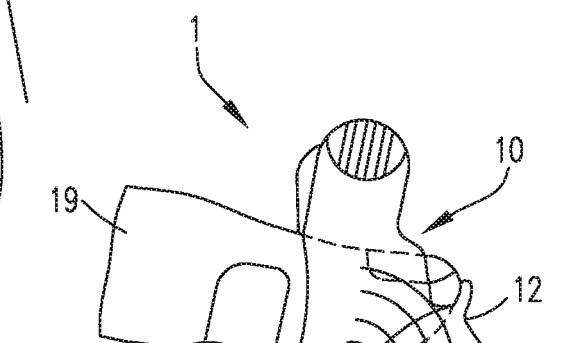
FIG. 5 is a perspective view of a vibration device attached to a blood collection device with a collection container attached to a holder in accordance with an embodiment of the present invention.
Figure 23:
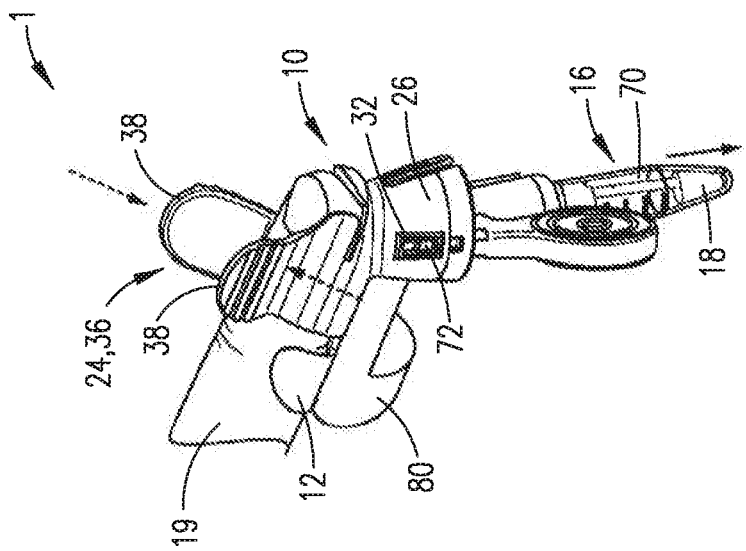
FIG. 23 is a perspective view of a third step of using a vibration device and blood collection device of the present disclosure in accordance with an embodiment of the present invention.
Figure 24:
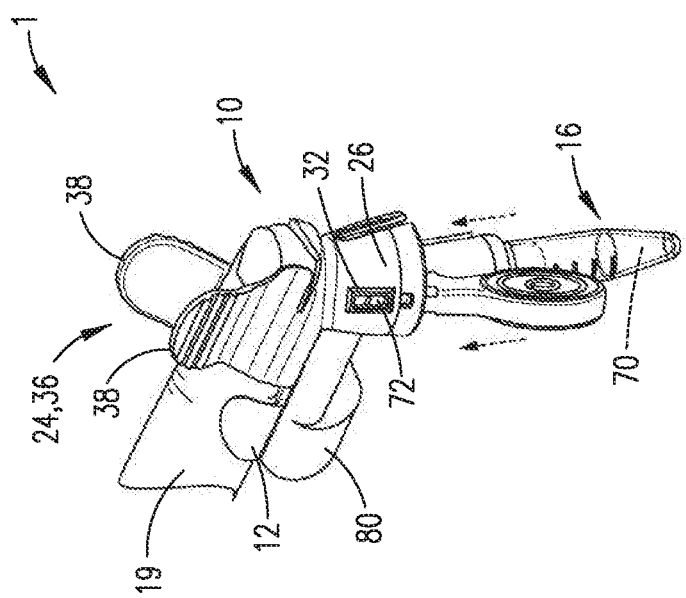
FIG. 24 is a perspective view of a fourth step of using a vibration device and blood collection device of the present disclosure in accordance with an embodiment of the present invention.

Referring to FIGS. 5, 23, and 24, by having the vibration device 80 turned on and providing vibrations to the blood collection device 10 and the finger 19 of the patient simultaneously with a user repeatedly squeezing and releasing the wings 38 of the holder 12 to pump and/or extract blood 18 from a finger 19 until a desired amount of blood 18 is filled in a collection container 16, the vibration signals sent to the finger 19 of the patient aid blood flow from the finger 19 into a collection container 16 during the collection process. For example, the mechanical vibrations from a vibration device 80 of the present disclosure in combination with controlled gentle finger massaging using a blood collection device of the present disclosure reduces patient discomfort during a blood extraction process as well as speeds up the collection by stimulating an efficient blood flow through the capillary beds and out of the finger.

Figure 6:
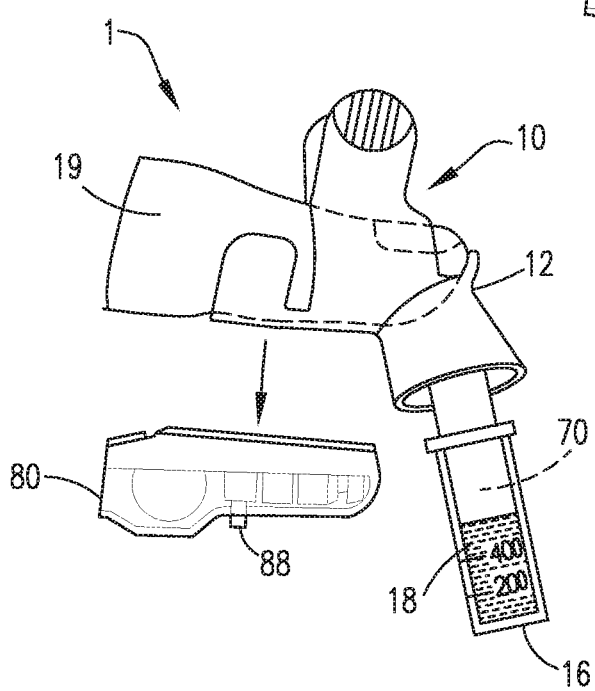
FIG. 6 is a perspective view of a vibration device removed from a blood collection device with a collection container attached to a holder in accordance with an embodiment of the present invention.

Referring to FIG. 6, the vibration device 80 is detached from the holder 12 of the blood collection device 10 before the collection device 10 is removed from the finger 19 for further blood sample processing. As discussed above, the vibration device 80 may then be reused with additional blood collection devices and the used blood collection device 10 may be properly disposed of.

Referring to FIGS. 1, 4-6, and 8, in one exemplary embodiment, a blood collection device 10 includes separate components, e.g., a holder 12, a lancet housing or lancet 14, and a collection container 16.

Figure 8:
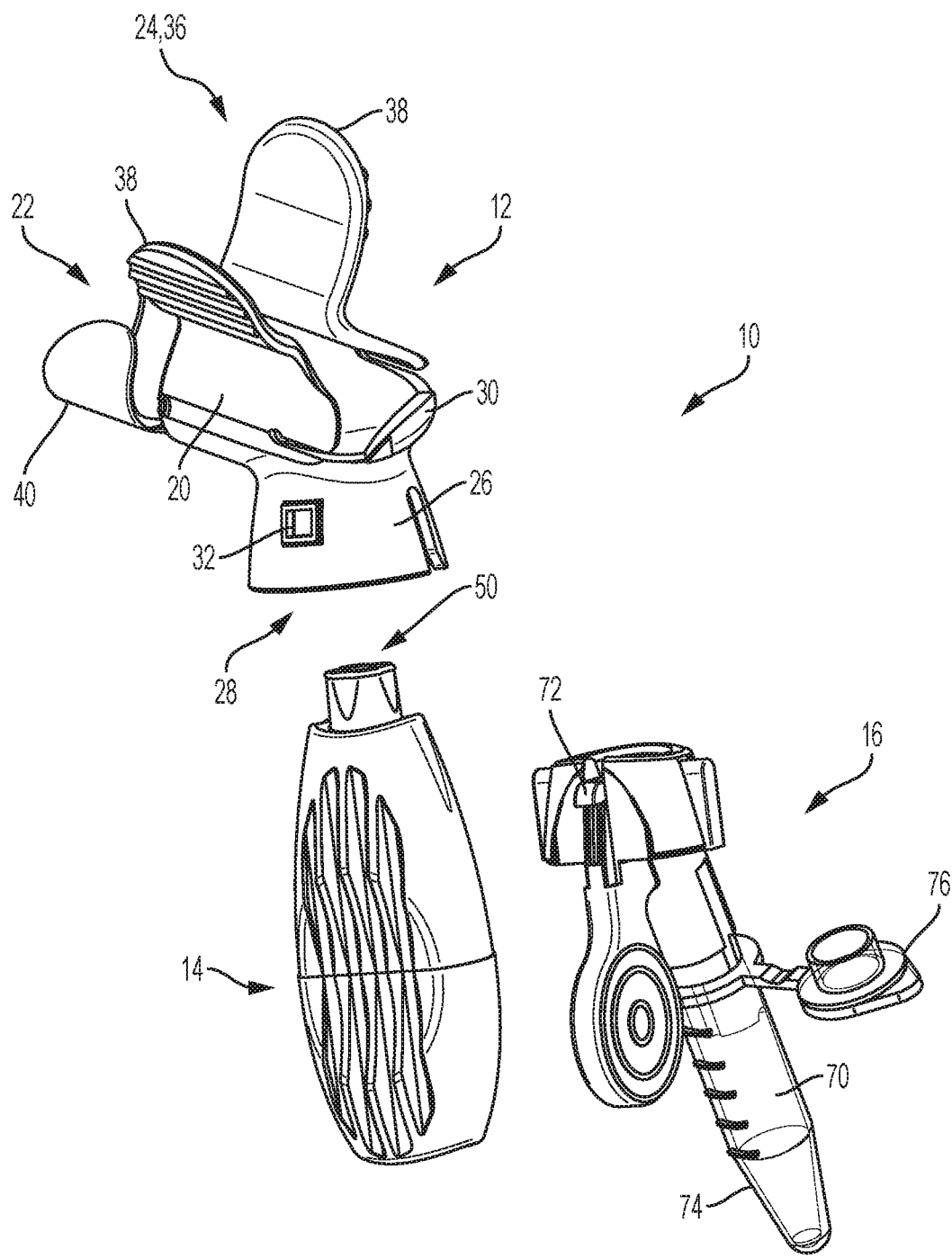
FIG. 8 is an exploded, perspective view of a blood collection device having discrete components for obtaining a blood sample in accordance with an embodiment of the present invention.
Figure 9:
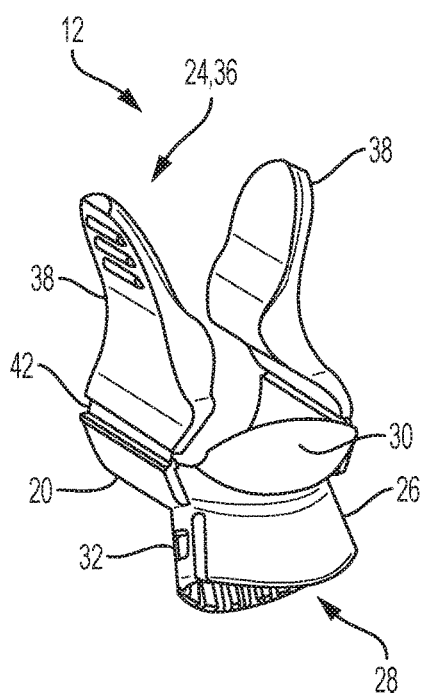
FIG. 9 is a perspective view of a holder in accordance with an embodiment of the present invention.
Figure 10:
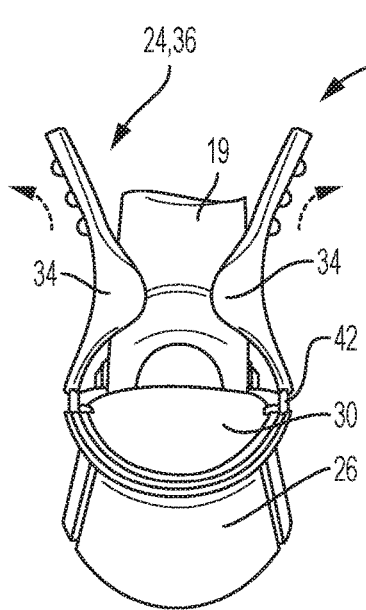
FIG. 10 is a perspective view of a holder in a first position in accordance with an embodiment of the present invention.
Figure 11:
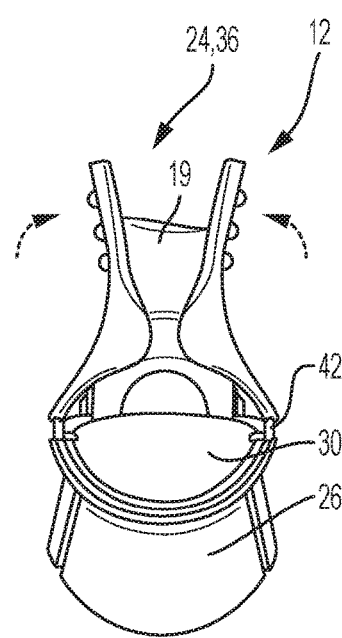
FIG. 11 is a perspective view of a holder in a second position in accordance with an embodiment of the present invention.

FIGS. 9-11 illustrate an exemplary embodiment of holder 12 that is compatible with the vibration device 80, as discussed herein. The holder 12 is able to receive a sample source, e.g., a finger 19, for supplying a biological sample, such as a blood sample 18. A holder 12 of the present disclosure generally includes a finger receiving portion 20 having a first opening 22 (FIGS. 8 and 12), an actuation portion 24, a port 26 having a second opening 28, and a finger end guard 30. In one embodiment, the finger end guard 30 provides a stop portion for properly aligning and securing a finger 19 within the holder 12.

The first opening 22 of the finger receiving portion 20 is configured for receiving a sample source, e.g., a finger 19, for supplying a biological sample, such as a blood sample 18. It can be appreciated that the sample source could include other parts of the body capable of fitting within the first opening 22. The port 26 is in communication with the finger receiving portion 20. For example, with a finger 19 received within the holder 12, the port 26 is in communication with a portion of the finger 19. A holder 12 of the present disclosure can be sized to accommodate all finger sizes.

In one embodiment, the finger receiving portion 20 is formed of a flexible material. In some embodiments, the finger receiving portion 20 and the port 26 are formed from a flexible material.

The second opening 28 of the port 26 is configured for receiving a lancet housing 14 and a collection container 16 as described in more detail below. In one embodiment, the port 26 includes a locking portion 32 for securely receiving the lancet housing 14 and the collection container 16 within the port 26.

In one embodiment, the actuation portion 24 is transitionable between a first position (FIG. 10) in which the holder 12 defines a first diameter and a second position (FIG. 11) in which the holder 12 defines a second diameter, wherein the second diameter is less than the first diameter. In one embodiment, the actuation portion 24 is transitionable between a first position (FIG. 10) in which the holder 12 defines a first elliptical shape, and a second position (FIG. 11) in which the holder 12 defines a second elliptical shape, wherein the first elliptical shape is different than the second elliptical shape. In this manner, with the holder 12 in the second position with a reduced diameter, a portion of the holder 12 contacts the sample source, e.g., finger 19, and the actuation portion 24 of the holder 12 is able to pump and/or extract blood 18 as described in more detail below.

Referring to FIGS. 10 and 11, in one embodiment, the actuation portion 24 includes a contact member 34. Referring to FIG. 10, with the actuation portion 24 in the first position, the contact member 34 is in a disengaged position, i.e., the contact member 34 is provided in a first position with respect to a sample source, e.g., the finger 19, such that the contact member 34 may be in slight contact therewith. Referring to FIG. 11, with the actuation portion 24 in the second position, the contact member 34 is in an engaged position, i.e., the contact member 34 is provided in a second position with respect to the sample source, e.g., the finger 19, such that the contact member 34 is in an applied pressure contact with the finer 19, and the actuation portion 24 of the holder 12 is able to pump and/or extract blood 18. For example, with the contact member 34 in the engaged position, the contact member 34 exerts a pressure on the sample source.

Referring to FIGS. 10 and 11, in one embodiment, the actuation portion 24 includes a pumping member 36 for applying pressure to the sample source, e.g., the finger 19. In one embodiment, the pumping member 36 comprises a pair of opposed tabs or wings 38. In such an embodiment, each tab 38 may include a contact member 34. Referring to FIGS. 9-11, in one embodiment, the holder 12 includes a living hinge portion 42. The living hinge portion 42 allows a user to squeeze the wings 38 between a first position (FIG. 10) and a second position (FIG. 11).

Advantageously, the holder 12 of the present disclosure allow a user to repeatedly squeeze and release the wings 38 to pump and/or extract blood 18 from a finger 19 until a desired amount of blood 18 is filled in a collection container 16.

Advantageously, with the holder 12 placed onto a finger 19, the holder 12 does not constrict the blood flow and defines lancing and finger squeezing locations. The squeezing tabs or wings 38 provide a pre-defined range of squeezing pressure that is consistently applied throughout a finger 19. By doing so, the holder 12 provides a gentle controlled finger massage that stimulates blood extraction and minimizes any potential hemolysis.

In one embodiment, the holder 12 includes a stability extension portion 40. This provides additional support for the holder 12 to be securely placed onto a finger 19. In one embodiment, the finger receiving portion 20 forms a generally C-shaped member and includes a plurality of inner gripping members for providing additional grip and support for the holder 12 to be securely placed onto a finger 19.

In other exemplary embodiments, the holder 12 of the present disclosure may be formed substantially similar to the holder structures described in PCT/US2017/048143, filed Aug. 23, 2017, entitled "A Device for Obtaining a Blood Sample", the entire disclosure of which is hereby expressly incorporated herein by reference.

In one exemplary embodiment, a blood collection device 10 of the present disclosure includes a lancet housing or lancet 14 that is removably connectable to a port 26 of a holder 12. Referring to FIGS. 4, 8, and 12-19, in one embodiment, the lancet housing 14 includes an inlet or opening 50, an interior 52, a puncturing element 54, an engagement portion 56, a retractable mechanism 58, and a drive spring 60. In one embodiment, the puncturing element 54 is moveable between a pre-actuated position wherein the puncturing element 54 is retained within the interior 52 of the lancet housing 14 and a puncturing position wherein at least a portion of the puncturing element 54 extends through the inlet 50 of the lancet housing 14 to lance a portion of a finger 19.

In one embodiment, the lancet 14 of the present disclosure is a contact activated lancet and may be constructed in accordance with the features disclosed in U.S. Patent Application Publication No. 2006/0052809 filed May 6, 2005, entitled "Contact Activated Lancet Device", and commonly assigned with the present application, the entire disclosure of which is hereby expressly incorporated herein by reference thereto.

Figure 4:
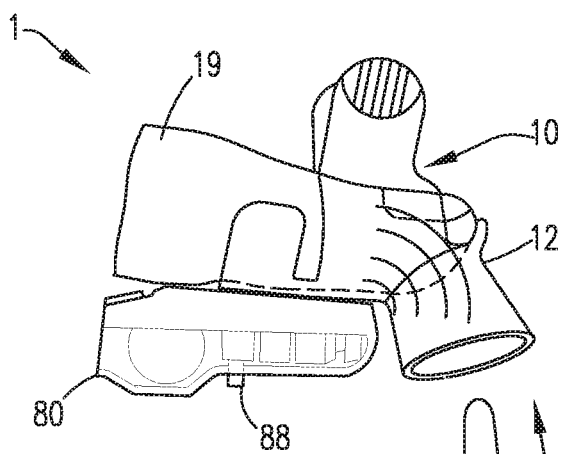
FIG. 4 is a perspective view of a vibration device attached to a blood collection device with a lancet being attached to a holder in accordance with an embodiment of the present invention.
Figure 12:
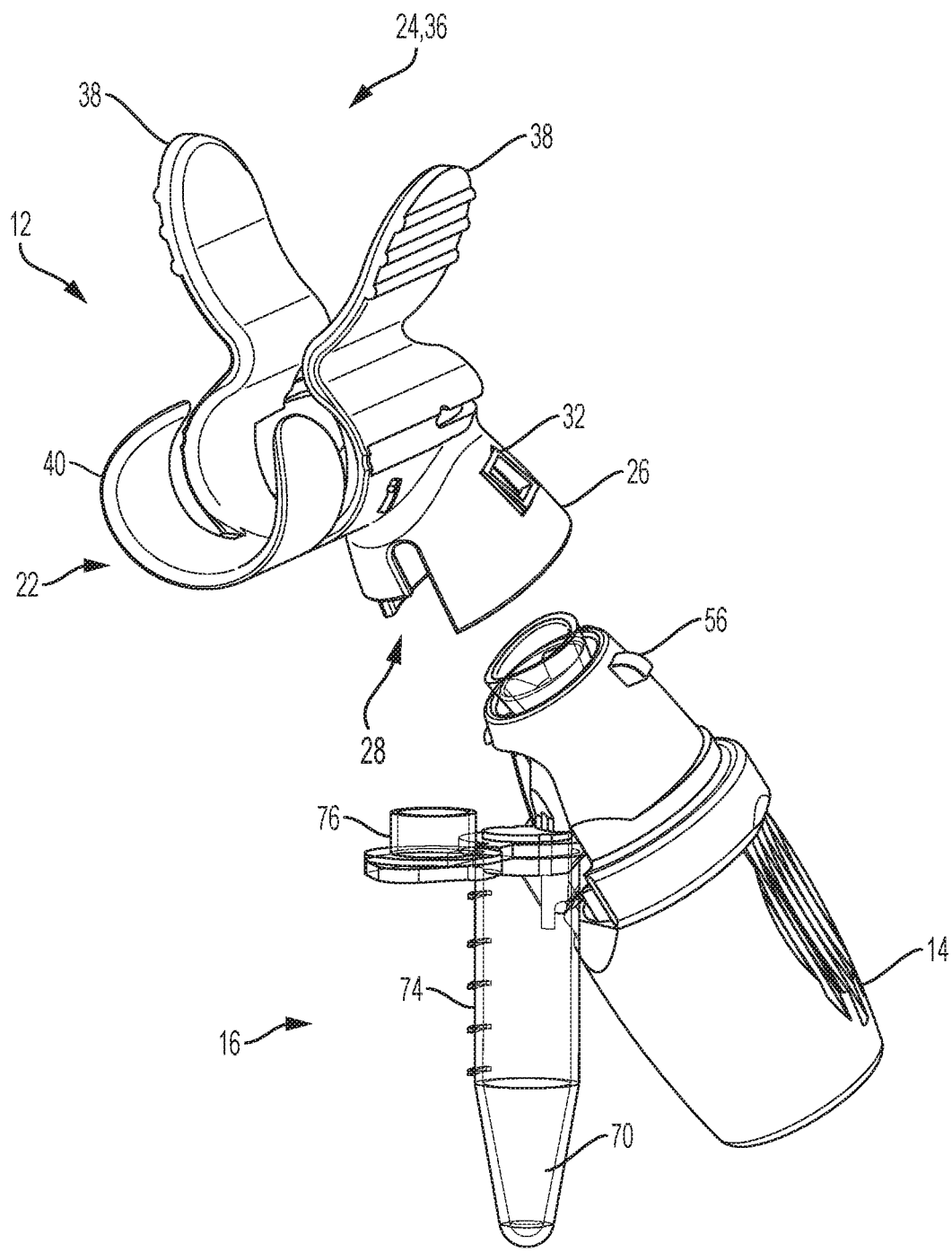
FIG. 12 is a perspective view of a semi-integrated blood collection device for obtaining a blood sample with an at-angle flow in accordance with another embodiment of the present invention.
Figure 13:
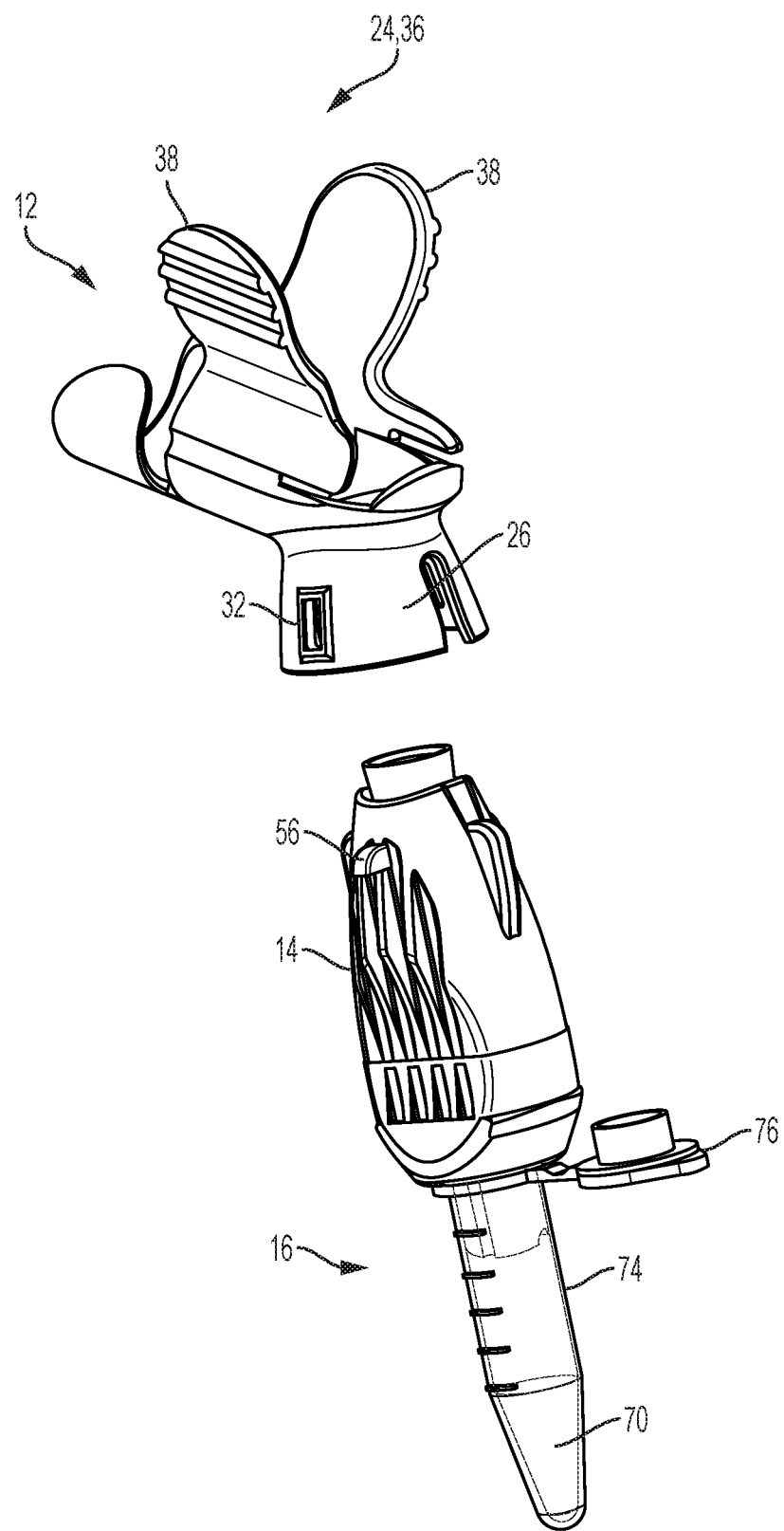
FIG. 13 is a perspective view of a semi-integrated blood collection device for obtaining a blood sample with an in-line flow in accordance with another embodiment of the present invention.

Referring to FIGS. 4 and 8, in one embodiment, the lancet housing 14 may be a separate component from the holder 12 and the collection container 16. Referring to FIGS. 12 and 13, in some embodiments, the collection container 16 and the lancet housing 14 form a single component that is removably connectable to the port 26 of the holder 12. Referring to FIGS. 2, 3, 15, and 17, in some embodiments, the collection container 16, the lancet housing 14, and the holder 12 form a single component.

Figure 14:
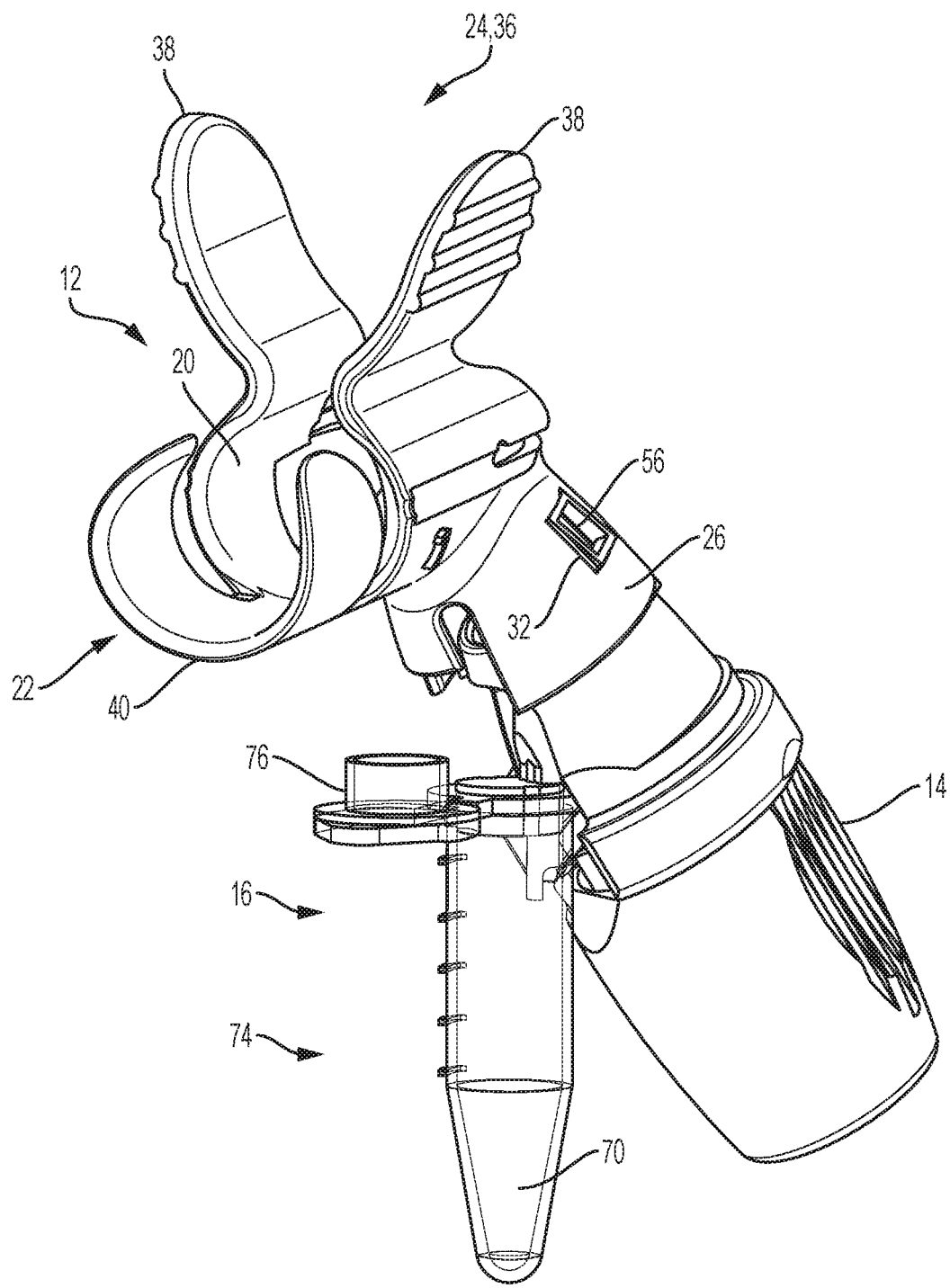
FIG. 14 is a perspective view of an integrated blood collection device for obtaining a blood sample with an at-angle flow in accordance with another embodiment of the present invention.
Figure 15:
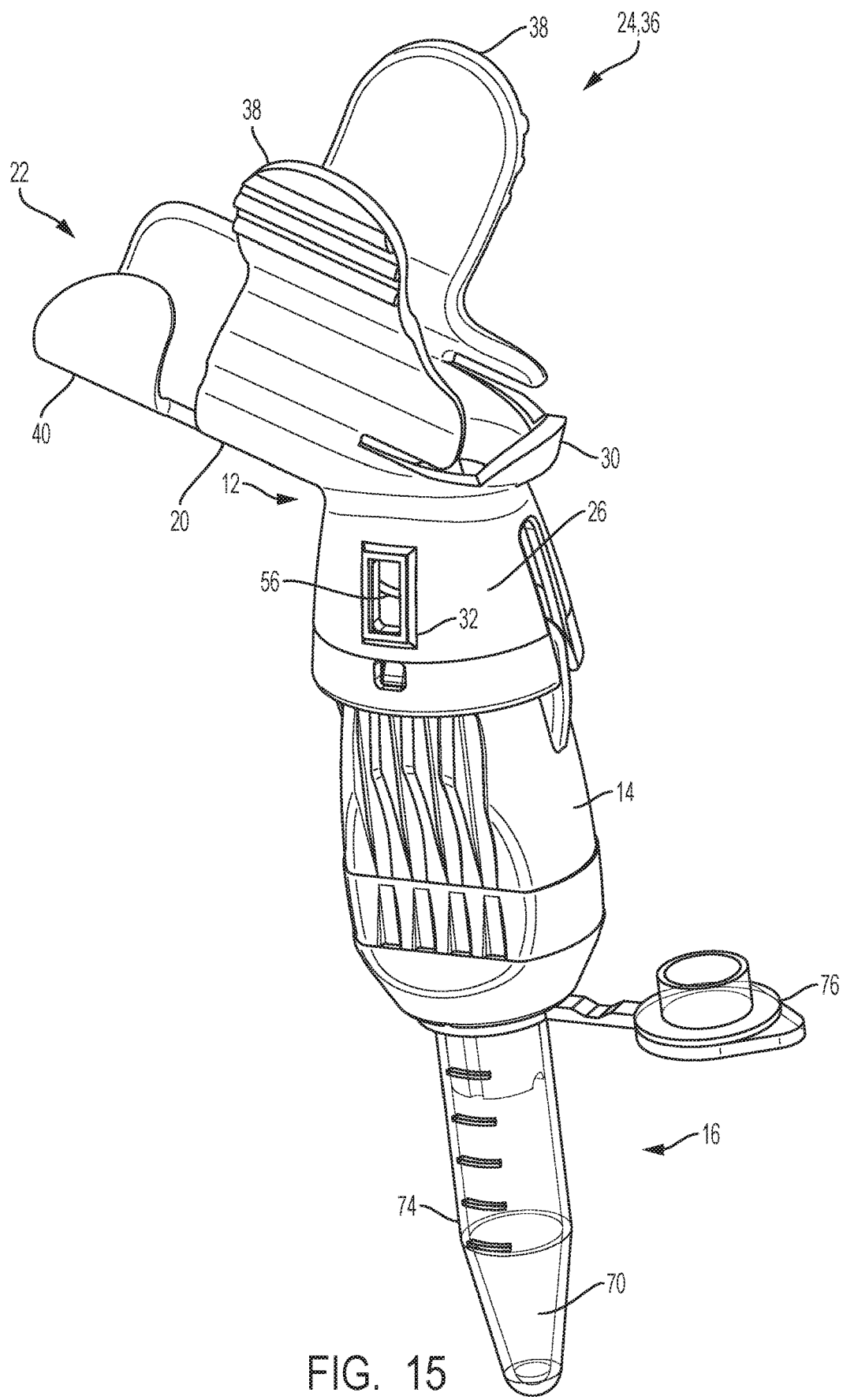
FIG. 15 is a perspective view of an integrated blood collection device for obtaining a blood sample with an in-line flow in accordance with another embodiment of the present invention.

Referring to FIGS. 4 and 8, in one embodiment, with the holder 12 and the lancet housing 14 being separate components, the lancet housing 14 is removably connectable to the port 26 of the holder 12. In such an embodiment, the lancet housing 14 includes an engagement portion 56. Referring to FIGS. 14 and 15, in one embodiment, the lancet housing 14 is pushed into the port 26 of the holder 12 such that the engagement portion 56 of the lancet housing 14 is locked within the locking portion 32 of the holder 12. In this manner, the lancet housing 14 is securely connected and locked to the holder 12 such that the puncturing element 54 of the lancet housing 14 can be activated to lance or puncture a sample source, e.g., a finger 19. In some embodiments, the port 26 of the holder 12 includes a plurality of ribs for securing and locking the lancet 14 or the collection container 16 in the port 26.

To activate the lancet 14, the lancet 14 is pushed against a finger 19 to activate a retractable mechanism 58 of the lancet 14 to lance a finger 19. The lancet 14 of the present disclosure consistently delivers correct lancing depth and a pre-defined lancing location, thus ensuring a sufficient sample volume.

In one embodiment, the lancet 14 includes a drive spring 60 disposed within the interior 52 of the lancet housing 14 for biasing the puncturing element 54 toward the puncturing position. After puncturing, the puncturing element 54 is immediately retracted and safely secured within the interior 52 of the lancet housing 14.

Referring to FIGS. 4 and 8, in one embodiment, the lancet 14 of the present disclosure is used to lance the skin of a finger 19 and then a blood sample 18 is squeezed into a collection container 16 as described in more detail below.

Figure 18:
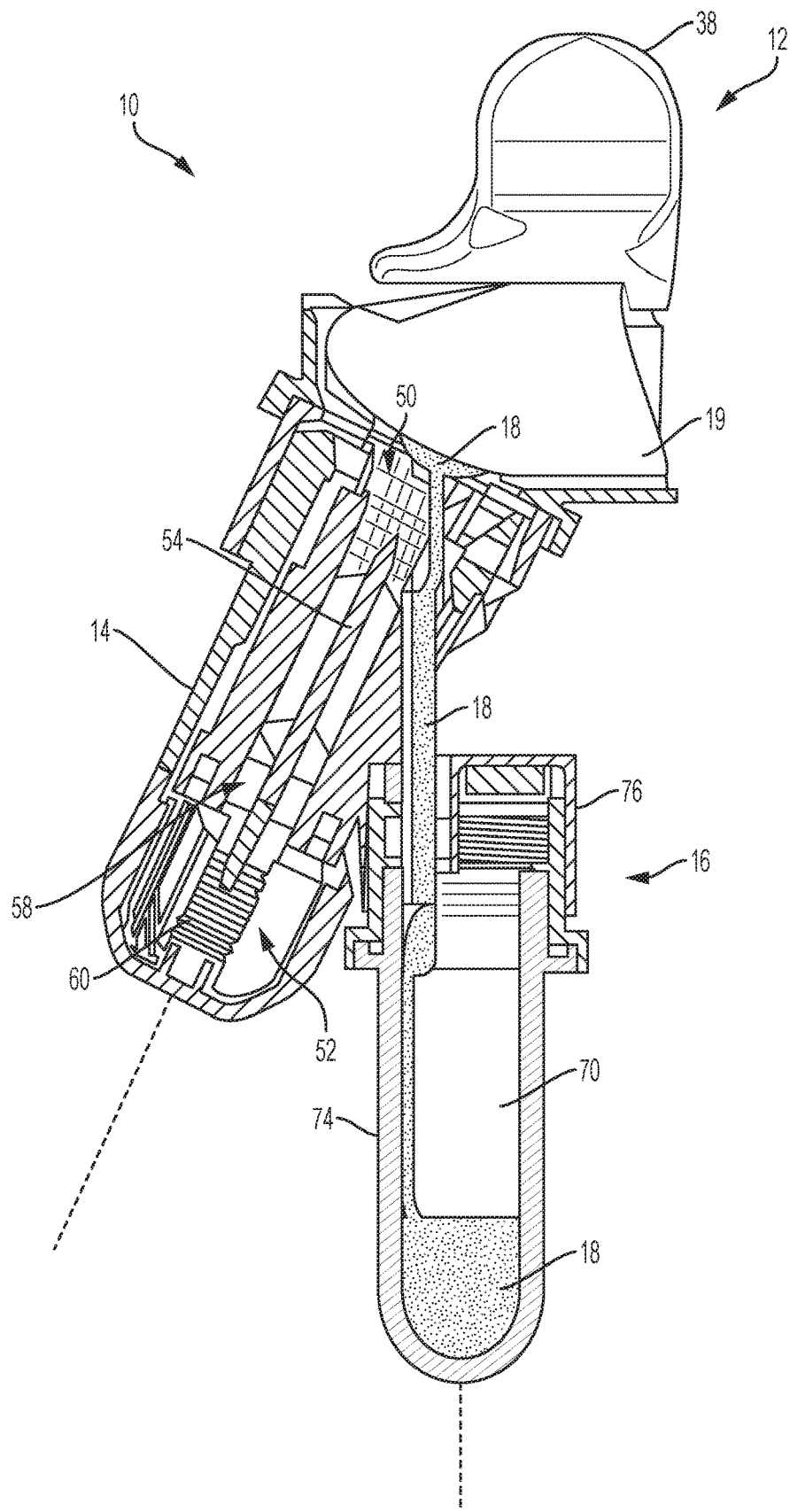
FIG. 18 is a cross-sectional view of a blood collection device of FIG. 14 showing a blood flow path in accordance with another embodiment of the present invention.
Figure 19:
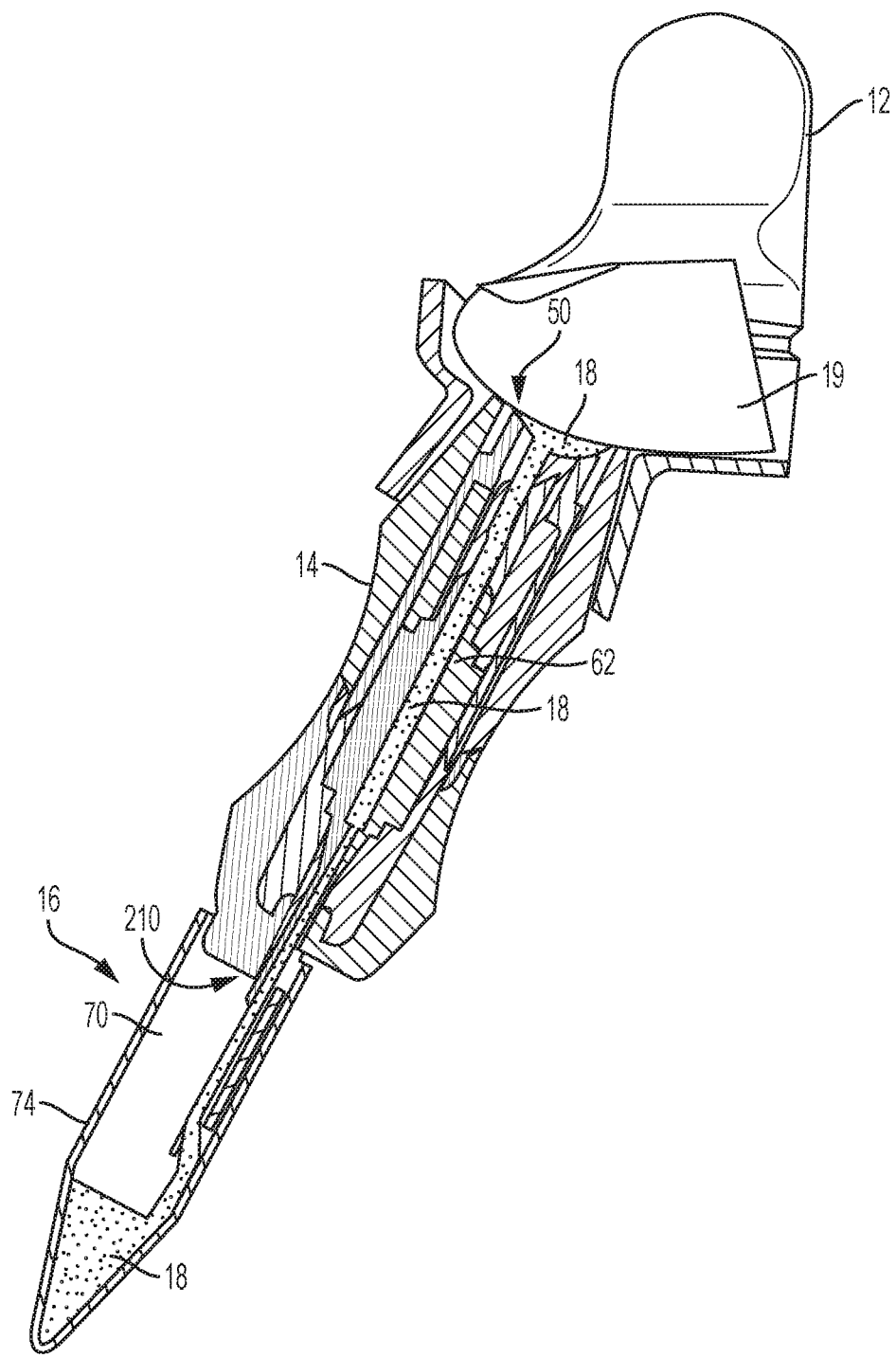
FIG. 19 is a cross-sectional view of a blood collection device of FIG. 15 showing a blood flow path in accordance with another embodiment of the present invention.

Referring to FIG. 18, in one embodiment, the lancet housing 14 of the present disclosure is used to lance the skin of a finger 19 along a lance path and then a blood sample 18 flows down a blood flow path at an angle to the lance path. Referring to FIG. 19, in one embodiment, the lancet 14 includes a hollow needle 62. In such an embodiment, the lancet housing 14 of the present disclosure is used to lance the skin of a finger 19 along a lance path and then a blood sample 18 flows along a parallel blood flow path through the hollow needle 62.

Figure 17:
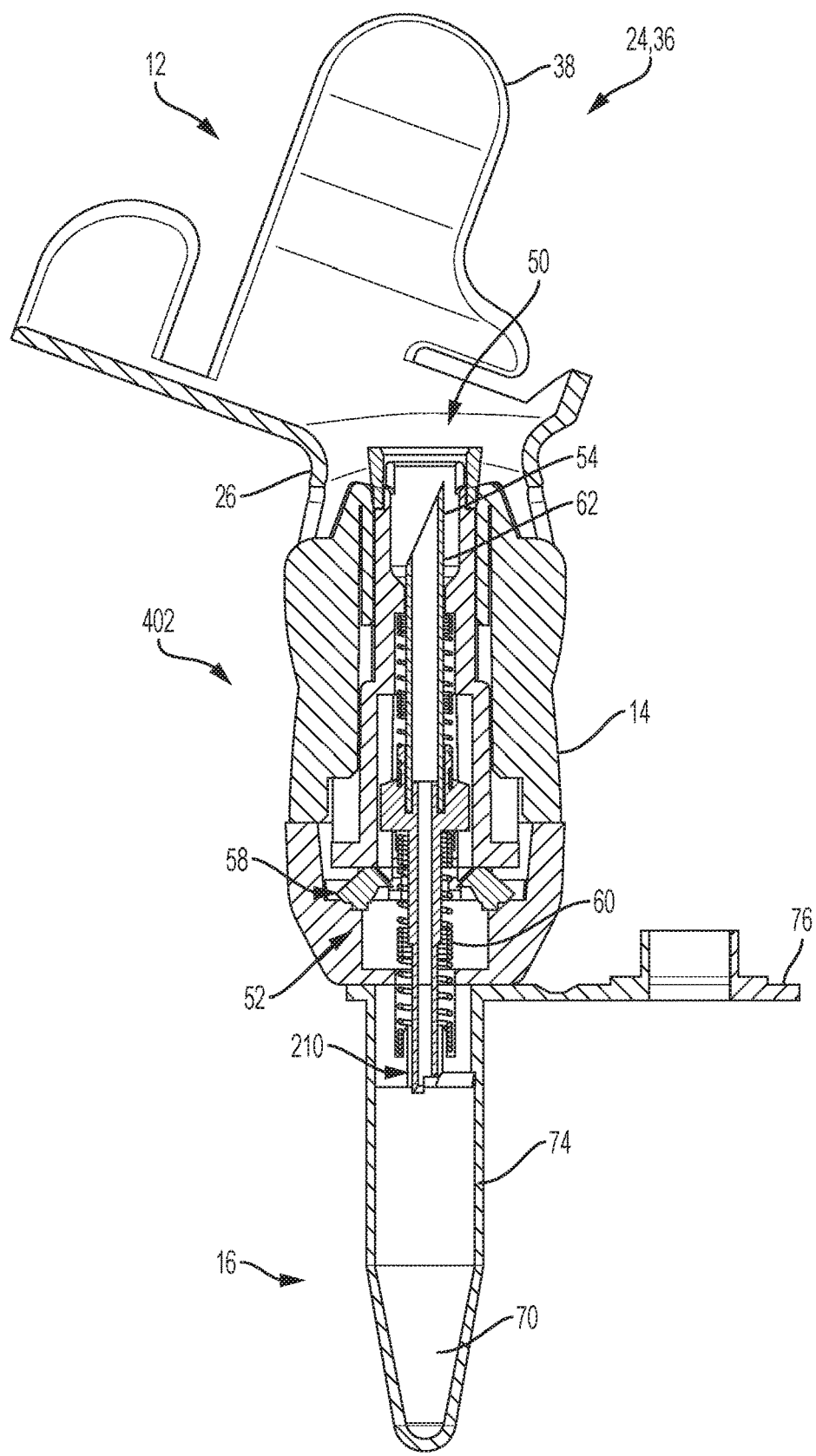
FIG. 17 is a cross-sectional view of a blood collection device of FIG. 15 in accordance with another embodiment of the present invention.

Referring to FIGS. 15, 17, and 19, in one embodiment, the lancet 14 includes a hollow needle 62. In such an embodiment, the lancet housing 14 of the present disclosure is used to lance the skin of a finger 19 along a lance path and then a blood sample 18 flows along a parallel blood flow path through the hollow needle 62. In one embodiment, the lancet housing 14 includes an outlet 210. With the container 16 connected to the lancet housing 14, the outlet 210 of the lancet housing 14 is in fluid communication with the collection cavity 70 of the container 16.

The lancet structures 14 and blood flow paths of the present disclosure may be formed substantially similar to the lancet structures and blood flow paths described in PCT/US2017/048143, filed Aug. 23, 2017, entitled "A Device for Obtaining a Blood Sample", the entire disclosure of which is hereby expressly incorporated herein by reference.

In one exemplary embodiment, a blood collection device 10 of the present disclosure includes a collection container 16 that is removably connectable to the port 26 of the holder 12. The collection container 16 defines a collection cavity 70 for receiving a blood sample 18, a container engagement portion 72, a blood collector portion 74, and a cap or septum 76. Once a desired amount of blood 18 is collected within the container 16, a blood collector portion 74 is detached from the blood collection device 10 in order to send a collected sample 18 to a diagnostic instrument and/or testing device. The blood collector portion 74 is sealed via the cap or septum 76 once removed from the collection device 10 to protectively seal the blood sample 18 within the collection cavity 70.

Referring to FIGS. 5 and 8, in one embodiment, the collection container 16 may be a separate component from the holder 12 and the lancet housing 14. Referring to FIGS. 12 and 13, in some embodiments, the collection container 16 and the lancet housing 14 form a single component that is removably connectable to the port 26 of the holder 12. Referring to FIGS. 2, 3, 15, and 17, in some embodiments, the collection container 16, the lancet housing 14, and the holder 12 form a single component.

Figure 20:
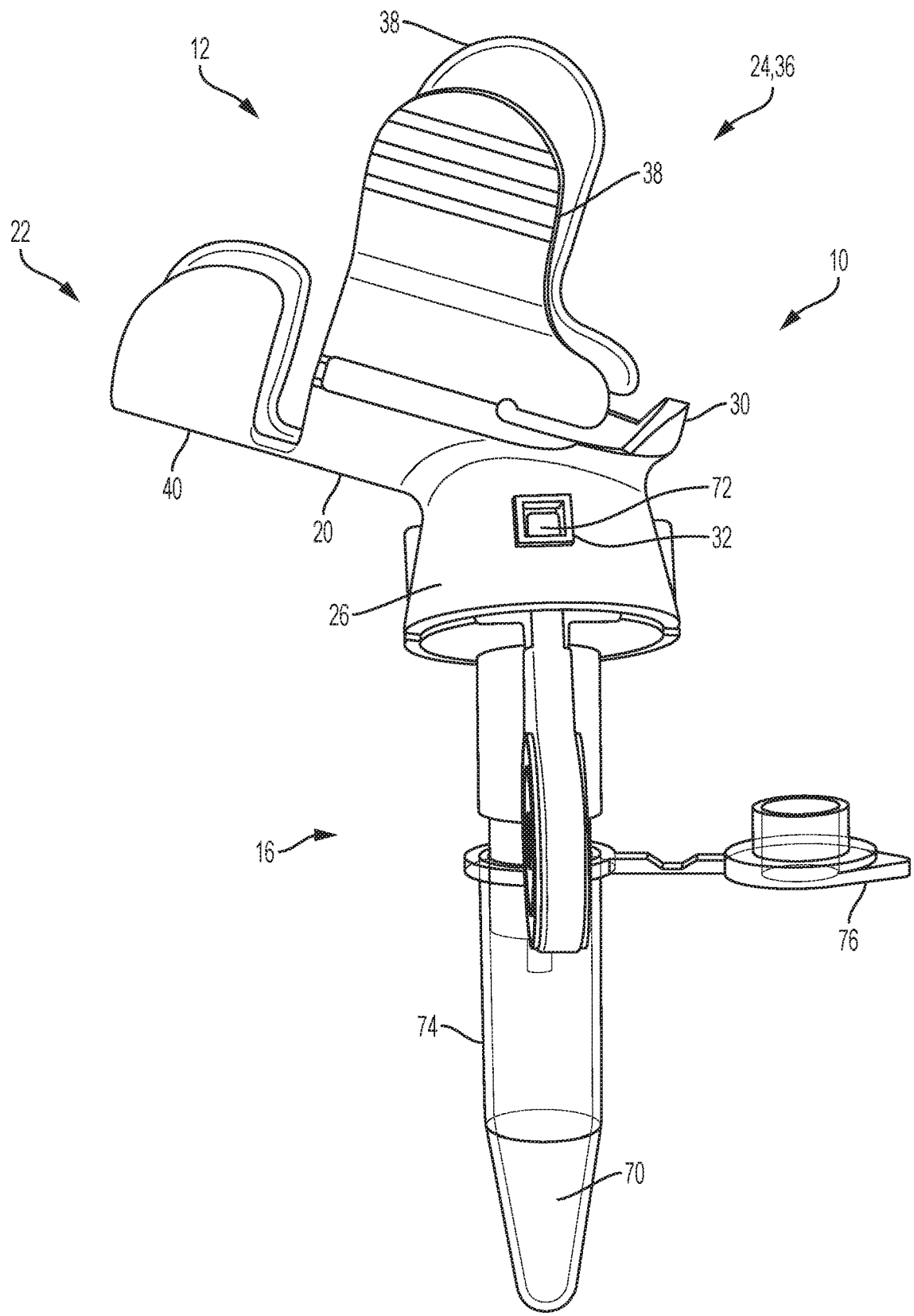
FIG. 20 is a perspective view of a holder with a container secured within a port in accordance with an embodiment of the present invention.

Referring to FIGS. 5 and 8, in one embodiment, with the holder 12 and the collection container 16 being separate components, the container 16 is removably connectable to the port 26 of the holder 12. In such an embodiment, the container 16 includes a container engagement portion 72. Referring to FIG. 20, in one embodiment, the container 16 is pushed into the port 26 of the holder 12 such that the container engagement portion 72 of the container 16 is locked within the locking portion 32 of the holder 12. In this manner, the container 16 is securely connected and locked to the holder 12 such that a blood sample 18 can safely flow from the finger 19 within the holder 12 to the collection cavity 70 of the container 16.

It can be appreciated that several types of collection containers 16 can be used with the device 10 of the present disclosure. It can also be appreciated that the collection container 16 can be associated with a separate dispensing unit or the collection container 16 can include an integral dispensing portion for dispensing the blood 18 to a testing device.

Referring to FIGS. 2-6 and 21-25, use of a vibration device 80 of the present disclosure with a blood collection device 10 having discrete components, e.g., a holder 12, a lancet housing or lancet 14, and a collection container 16, will now be described.

Referring to FIG. 2, in one embodiment, the vibration device 80 is attached to the blood collection device 10 before the holder 12 of the blood collection device 10 is placed onto a finger 19 of a patient. Next, referring to FIG. 21, a desired finger 19 is cleaned and a holder 12 having an appropriate size for the desired finger 19 is selected and placed onto the finger 19 securely with the vibration device 80 attached to the blood collection device 10. Next, referring to FIG. 22, a lancet housing 14 is connected to the port 26 of the holder 12. As discussed above, the lancet housing 14 is pushed into the port 26 of the holder 12 such that the engagement portion 56 of the lancet housing 14 is locked within the locking portion 32 of the holder 12. In this manner, the lancet housing 14 is securely connected and locked to the holder 12 such that the puncturing element 54 (FIGS. 16-18) of the lancet housing 14 can be activated to lance or puncture a sample source, e.g., a finger 19. With the lancet 14 connected to the port 26 of the holder 12, the lancet is in communication with the finger 19.

Next, referring to FIGS. 4, 21, and 22, the vibration device 80 is turned to the on position to vibrate the blood collection device 10 and the finger 19 of the patient before lancing the finger 19 using the puncturing element 54 of the lancet 14. The vibration device 80 is kept on to provide vibrations to the blood collection device 10 and the finger 19 of the patient until the blood collection is completed. For example, referring to FIG. 22, by having the vibration device 80 turned on and providing vibrations to the blood collection device 10 and the finger 19 of the patient simultaneously with the puncturing element 54 (FIGS. 16-18) of the lancet 14 cutting the finger 19 of the patient causing sharp pain, the vibration signals sent to the finger 19 of the patient and the pain nerve signals from the lancet cut are mixed together. In this manner, the vibration signals are able to mask the overall pain signal to the brain, provide a different sensation experience, and often a perception of lower pain thereby providing a patient pain relief during finger lancing.

Referring to FIG. 22, when it is desired to activate the lancet 14 to lance the skin of a finger 19, the lancet 14 is pushed against a finger 19 to activate a retractable mechanism 58 (FIGS. 16-18) of the lancet 14 to lance a finger 19. The lancet 14 of the present disclosure consistently delivers correct lancing depth and a pre-defined lancing location, thus ensuring a sufficient sample volume.

After the finger 19 is lanced to create blood 18 (FIG. 24) flow from the finger 19, the lancet 14 is removed from the holder 12 and the collection container 16 is pushed into the port 26 of the holder 12. Referring to FIG. 23, the container 16 is pushed into the port 26 of the holder 12 such that the container engagement portion 72 of the container 16 is locked within the locking portion 32 of the holder 12. In this manner, the container 16 is securely connected and locked to the holder 12 such that a blood sample 18 can safely flow from the finger 19 within the holder 12 to the collection cavity 70 of the container 16.

Referring to FIGS. 23 and 24, with the container 16 properly secured to the holder 12 for collection of a blood sample 18, a user is able to repeatedly squeeze and release the wings 38 of the holder 12 to pump and/or extract blood 18 from a finger 19 until a desired amount of blood 18 is filled in a collection container 16. Advantageously, with the holder 12 placed onto a finger 19, the holder 12 does not constrict the blood flow and defines lancing and finger squeezing locations.

The squeezing tabs or wings 38 provide a pre-defined range of squeezing pressure that is consistently applied throughout a finger 19. By doing so, the holder 12 provides a gentle controlled finger 19 massage that stimulates blood extraction and minimizes any potential hemolysis.

For example, referring to FIGS. 10 and 11, in one embodiment, the actuation portion 24 includes a contact member 34. Referring to FIG. 10, with the actuation portion 24 in the first position, the contact member 34 is in a disengaged position, i.e., the contact member 34 is in the first position with respect to the sample source, e.g., the finger 19. Referring to FIG. 11, with the actuation portion 24 in the second position, the contact member 34 is in an engaged position, i.e., the contact member 34 is in the second position and in applied pressure contact with a sample source, e.g., the finger 19, and the actuation portion 24 of the holder 12 is able to pump and/or extract blood 18. For example, with the contact member 34 in the engaged position, the contact member 34 exerts a pressure on the sample source.

Referring to FIGS. 5, 23, and 24, by having the vibration device 80 turned on and providing vibrations to the blood collection device 10 and the finger 19 of the patient simultaneously with a user repeatedly squeezing and releasing the wings 38 of the holder 12 to pump and/or extract blood 18 from a finger 19 until a desired amount of blood 18 is filled in a collection container 16, the vibration signals sent to the finger 19 of the patient aid blood flow from the finger 19 into a collection container 16 during the collection process. For example, the mechanical vibrations from a vibration device 80 of the present disclosure in combination with controlled gentle finger massaging using a blood collection device of the present disclosure reduces patient discomfort during a blood extraction process as well as speeds up the collection by stimulating an efficient blood flow through the capillary beds and out of the finger.

Referring to FIG. 6, the vibration device 80 is detached from the holder 12 of the blood collection device 10 before the collection device 10 is removed from the finger 19 for further blood sample processing.

Figure 25:
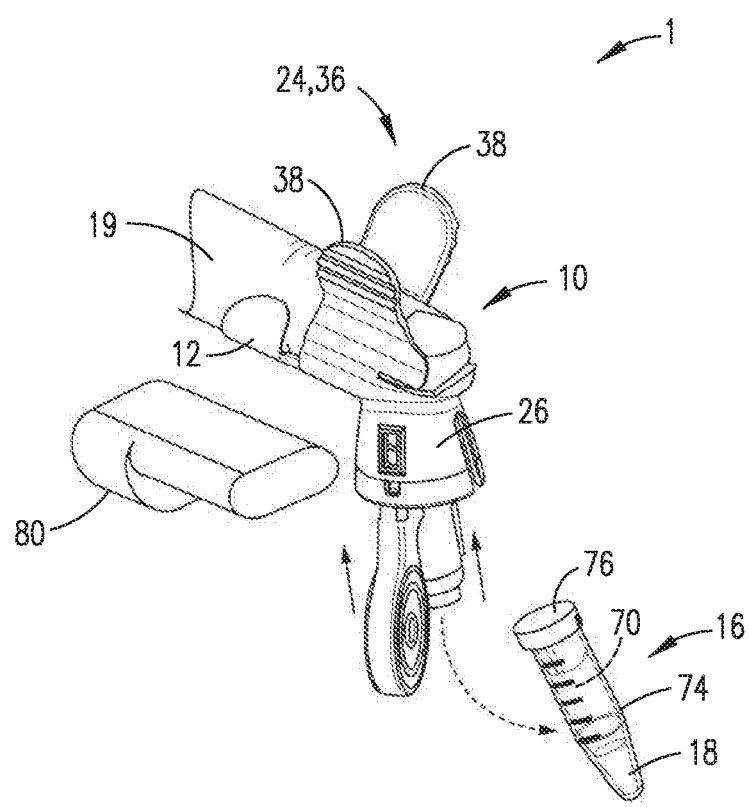
FIG. 25 is a perspective view of a fifth step of using a vibration device and blood collection device of the present disclosure in accordance with an embodiment of the present invention.

Referring to FIG. 25, once the vibration device 80 is removed and a desired amount of blood 18 is collected within the container 16, a blood collector portion 74 is detached from the collection device 10 in order to send a collected sample 18 to a diagnostic instrument and/or testing device. The blood collector portion 74 is sealed via the cap or septum 76 once removed from the collection device 10 to protectively seal the blood sample 18 within the collection cavity 70. As discussed above, the vibration device 80 may then be reused with additional blood collection devices and the used blood collection device 10 may be properly disposed of.

The devices of the present disclosure are compatible with any known testing device, whether the testing device is off-site or a point-of-care testing device. Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run, but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

The collection container 16 may also contain a sample stabilizer, e.g., an anticoagulant, to stabilize a blood sample and/or a component of a blood sample disposed therein. The collection container 16 may also include at least one fill line(s) corresponding to a predetermined volume of sample. The collection container may also indicate/meter a collected volume of blood.

As described above, referring to FIGS. 4-6 and 8, in one embodiment, the lancet housing 14 may be a separate component from the holder 12 and the collection container 16. Referring to FIGS. 12 and 13, in some embodiments, the collection container 16 and the lancet housing 14 form a single component that is removably connectable to the port 26 of the holder 12. Referring to FIGS. 2, 3, 15, and 17, in some embodiments, the collection container 16, the lancet housing 14, and the holder 12 form a single component. Use of these other exemplary embodiments of a blood collection device 10 with a vibration device 80 of the present disclosure includes similar steps to the steps described above with respect to FIGS. 21-25. When using a single component blood collection device 10, a user will not need to attach and remove a lancet housing 14 before attaching and removing a collection container 16.

Use of the blood collection device embodiments shown in FIGS. 12, 13, 15, and 17 may be used substantially similar to the devices described in PCT/US2017/048143, filed Aug. 23, 2017, entitled "A Device for Obtaining a Blood Sample", the entire disclosure of which is hereby expressly incorporated herein by reference.

A vibration device 80 and a blood collection device 10 of the present disclosure provide a device for obtaining a biological sample, such as a capillary blood collection device, which has the ability to lance and squeeze the finger while providing pain relief, collect the sample while aiding blood flow, stabilize the sample, and subsequently dispense the sample in a controlled manner. The device also simplifies and streamlines the capillary blood collection by eliminating workflow variabilities which are typically associated with low sample quality including hemolysis and micro-clots.

A vibration device of the present disclosure provides pain relief to a patient during use of a blood collection device by de-sensitizing skin via mechanical vibrations that stimulate Aβ peripheral nerve fibers and mask pain signals sent to the brain during a finger lancing process. Additionally, the mechanical vibrations in combination with controlled gentle finger massaging using a blood collection device of the present disclosure reduces patient discomfort during a blood extraction process as well as speeds up the collection by stimulating an efficient blood flow through the capillary beds and out of the finger.

Moreover, a vibration device of the present disclosure is a simple and low cost reusable device that also promotes blood flow through a blood collection device and into a collection container as well as promotes blood mixing with an anticoagulant.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An assembly for obtaining a blood sample, the assembly comprising:
   a blood collection device configured to removably receive a container having a collection cavity for receiving the blood sample, the blood collection device comprising:
      a holder for receiving a sample source that provides the blood sample, the holder having an actuation portion and a port;
      a lancet housing removably secured within the port, the lancet housing having an inlet and an interior; and
      a hollow puncturing element defining a flow path in fluid communication with the collection cavity of the container, the hollow puncturing element being moveable between a pre-actuated position in which the hollow puncturing element is retained within the interior and a puncturing position in which at least a portion of the hollow puncturing element extends through the inlet; and
   a vibration device removably attachable to the blood collection device configured such that, attaching the vibration device to the blood collection device activates the vibration device to vibrate an entirety of the blood collection device, and removing the vibration device from the blood collection device deactivates the vibration device.

2. The assembly of claim 1, wherein the vibration device is transitionable between an off position and an on position.

3. The assembly of claim 1, wherein the vibration device is attached to the blood collection device via a mechanical connection.

4. The assembly of claim 1, wherein the vibration device is attached to the blood collection device via a magnetic connection.

5. The assembly of claim 1, wherein a frequency of the vibration device is between 10 Hz and 1,000 Hz.

6. The assembly of claim 5, wherein the frequency of the vibration device is between 30 Hz and 120 Hz.

7. The assembly of claim 1, wherein the vibration device is configured to vibrate both an entirety of the device for obtaining the blood sample and a sample source before cutting, lancing, or puncturing the sample source.

8. The assembly of claim 1, wherein the container is configured to contain a large capillary sample of about 300 μL to 500 μL within the collection cavity.

9. A device for obtaining a blood sample, the device comprising:
   a holder for receiving a sample source, the holder having an actuation portion and a port;
   a lancet housing removably secured within the port, the lancet housing having an inlet and an interior;
   a hollow puncturing element defining a flow path, the hollow puncturing element being moveable between a pre-actuated position wherein the hollow puncturing element is retained within the interior and a puncturing position wherein at least a portion of the hollow puncturing element extends through the inlet;

a container removably connectable to a portion of the lancet housing, the container defining a collection cavity for receiving the blood sample from the flow path of the hollow puncturing element; and a vibration device removably connectable to a portion of the holder, wherein the vibration device is configured such that activation of the vibration device occurs when the vibration device is coupled with the holder of the device and deactivation of the vibration device occurs when the vibration device is decoupled from the holder of the device, and wherein the vibration device is configured such that, with the vibration device coupled to the holder, the vibration device vibrates an entirety of the holder, the lancet housing, the hollow puncturing element, the container, and the vibration device.

10. The device of claim 9, wherein the actuation portion is transitionable between a first position in which the holder at least partially encloses a first virtual elliptical shape and a second position in which the holder at least partially encloses a second virtual elliptical shape, and wherein a height and/or width of the second virtual elliptical shape is smaller than a height and/or width of the first virtual elliptical shape.

11. The device of claim 9, wherein the actuation portion includes a pumping member for applying pressure to the sample source.

12. The device of claim 11, wherein the pumping member comprises a pair of opposed tabs.

13. The device of claim 9, wherein the holder is configured to receive the sample source comprising a finger and the port is configured such that, with the finger received within the holder, the port is in communication with a portion of the finger.

14. The device of claim 9, wherein the vibration device is attached to the holder via a mechanical connection.

15. The device of claim 9, wherein the vibration device is attached to the holder via a magnetic connection.

16. The device of claim 9, wherein the vibration device is configured to vibrate the entirety of the holder, the lancet housing, the hollow puncturing element, the container, and the vibration device, and the sample source before cutting, lancing, or puncturing the sample source.

17. A device for obtaining a blood sample, the device comprising:

a holder for receiving a sample source, the holder having an actuation portion;

a vibration device removably connectable to a portion of the holder; and a container removably connectable to the holder, the container defining a collection cavity for receiving the blood sample, wherein the actuation portion is transitionable between a first position in which the holder at least partially encloses a first virtual elliptical shape and a second position in which the holder at least partially encloses a second virtual elliptical shape, wherein a height and/or width of the second virtual elliptical shape is smaller than a height and/or width of the first virtual elliptical shape, wherein the vibration device is configured such that activation of the vibration device occurs when the vibration device is coupled with the holder and deactivation of the vibration device occurs when the vibration device is decoupled from the holder, and wherein the vibration device is configured such that, with the vibration device coupled to the holder, the vibration device vibrates an entirety of the holder, the container, and the vibration device.

18. The device of claim 17, wherein the actuation portion includes a pumping member for applying pressure to the sample source.

19. The device of claim 17, wherein the vibration device is configured to vibrate both the entirety of the holder, the container, and the vibration device and the sample source before cutting, lancing, or puncturing the sample source.

20. An assembly for obtaining a blood sample, the assembly comprising:

a blood collection device configured to removably receive a container having a collection cavity for receiving the blood sample, the blood collection device comprising a holder for receiving a sample source that provides the blood sample, the holder having an actuation portion, wherein the actuation portion is transitionable between a first position in which the holder at least partially encloses a first virtual elliptical shape and a second position in which the holder at least partially encloses a second virtual elliptical shape, and wherein a height and/or width of the second virtual elliptical shape is smaller than a height and/or width of the first virtual elliptical shape; and a vibration device removably attachable to the blood collection device, wherein the vibration device is configured such that attaching the vibration device to the blood collection device activates the vibration device to vibrate an entirety of the blood collection device, and removing the vibration device from the blood collection device deactivates the vibration device.

21. The assembly of claim 20, wherein the vibration device is transitionable between an off position and an on position.

22. The assembly of claim 20, wherein the vibration device is attached to the blood collection device via a mechanical connection.

23. The assembly of claim 20, wherein the vibration device is attached to the blood collection device via a magnetic connection.

24. The assembly of claim 20, wherein a frequency of the vibration device is between 10 Hz and 1,000 Hz.

25. The assembly of claim 24, wherein the frequency of the vibration device is between 30 Hz and 120 Hz.

26. The assembly of claim 20, wherein the container is configured to contain a large capillary sample of about 300 µL to 500 µL within the collection cavity.

* * * * *

UNITED STATES PATENT AND TRADEMARK OFFICE
CERTIFICATE OF CORRECTION

| | | |
|---|---|---|
| PATENT NO. | : 12,329,523 B2 | Page 1 of 1 |
| APPLICATION NO. | : 17/057327 | |
| DATED | : June 17, 2025 | |
| INVENTOR(S) | : Milan Ivosevic et al. | |

It is certified that error appears in the above-identified patent and that said Letters Patent is hereby corrected as shown below:

In the Specification

Column 1, Line 8, delete "fed" and insert -- filed --

In the Claims

Column 16, Line 31, Claim 1, delete "that," and insert -- that --

Signed and Sealed this
Fifth Day of August, 2025

Coke Morgan Stewart
*Acting Director of the United States Patent and Trademark Office*